United States Patent
Mahameed et al.

(10) Patent No.: US 9,439,616 B2
(45) Date of Patent: Sep. 13, 2016

(54) NUCLEAR MEDICINE IMAGING SYSTEMS AND METHODS OF IMAGING PATIENT TISSUE

(71) Applicant: GE Medical Systems Israel, Ltd. (IL), Tirat Hacarmel (IL)

(72) Inventors: Riyad Mahameed, Tirat Carmel (IL); Michael Kogan, Tirat Hacarmel (IL); Raed Khamaisi, Tirat Hacarmel (IL)

(73) Assignee: GE Medical Systems Israel, Ltd. (IL), Tirat Hacarmel (IL)

( * ) Notice: Subject to any disclaimer, the term of this patent is extended or adjusted under 35 U.S.C. 154(b) by 172 days.

(21) Appl. No.: 14/167,702

(22) Filed: Jan. 29, 2014

(65) Prior Publication Data

US 2015/0208997 A1 Jul. 30, 2015

(51) Int. Cl.
*A61B 6/00* (2006.01)
*A61B 6/12* (2006.01)

(52) U.S. Cl.
CPC ............ *A61B 6/5205* (2013.01); *A61B 6/4258* (2013.01); *A61B 6/4266* (2013.01); *A61B 6/502* (2013.01); *A61B 6/12* (2013.01); *A61B 6/4057* (2013.01); *A61B 6/4447* (2013.01)

(58) Field of Classification Search
CPC .... A61B 6/12; A61B 6/4057; A61B 6/4258; A61B 6/4266; A61B 6/4447; A61B 6/502; A61B 6/5205
See application file for complete search history.

(56) References Cited

U.S. PATENT DOCUMENTS

| 2013/0131509 A1 | 5/2013 | Rafaeli et al. |
| 2013/0223590 A1 | 8/2013 | Rafaeli et al. |
| 2014/0093035 A1* | 4/2014 | Beekman ................. A61B 6/06 378/37 |

FOREIGN PATENT DOCUMENTS

NL    WO 2010014001 A2 *  2/2010 ........... G01T 1/1648

* cited by examiner

*Primary Examiner* — Michael Rozanski
(74) *Attorney, Agent, or Firm* — Dean D. Small; The Small Patent Law Group, LLC

(57) ABSTRACT

Nuclear medicine (NM) imaging system including first and second NM cameras having camera surfaces that are configured to face each other while imaging patient tissue therebetween. The NM imaging system also includes an immobilization plate that is configured to be positioned between the first and second NM cameras and extend parallel to the camera surface of the first NM camera. The immobilization plate is movable to and from the camera surface of the first NM camera to compress the patient tissue, and the second NM camera is movable to and from the immobilization plate. The second NM camera is oriented with respect to a roll axis that extends parallel to the immobilization plate. The second NM camera is rotatable about the roll axis while the immobilization plate and the first NM camera have fixed positions with respect to each other with the patient tissue therebetween.

20 Claims, 10 Drawing Sheets

NUCLEAR MEDICINE IMAGING SYSTEMS AND METHODS OF IMAGING PATIENT TISSUE

BACKGROUND

The subject matter disclosed herein relates generally to nuclear medicine (NM) imaging, and more particularly to methods and systems for determining a location of a lesion detected by NM imaging within a volume of space.

Various imaging techniques have been used for detection of cancerous lesions within a region of interest. For instance, mammography is the most common imaging technique used to detect lesions within breast tissue. If a lesion is suspected as being cancerous from a mammogram, a biopsy may be performed in which a sample of the lesion is extracted from the breast tissue using a biopsy needle. In many cases, an additional imaging modality, such as ultrasound, may be used to guide the biopsy needle toward the lesion and verify that an end of the biopsy needle is within the lesion.

For some individuals, such as those who have dense breast tissue or who have had prior surgery, mammograms alone may not be capable of sufficiently detecting lesions. One alternative for such individuals may be molecular breast imaging (MBI), which is also referred to as breast-specific gamma imaging (BGSI). MBI uses a dual-head gamma camera system to image the breast. During an MBI session, a radiopharmaceutical (e.g., Tc-99m sestamibi or other agent) is injected into the patient and absorbed by lesions existing within the breast. The breast is then positioned within a space between two nuclear medicine (NM) cameras. The NM cameras detect gamma radiation emitted by the radiopharmaceutical within the lesion(s).

MBI typically provides two-dimensional (2D) images of the breast tissue. A 2D location (e.g., X, Y coordinates) of the lesion may be identified using the 2D images, but a depth (e.g., Z coordinate) of the lesion within the breast tissue may not be determined by the 2D images. When the depth of the lesion is unknown, guidance of the biopsy needle may be difficult and the risk of missing the lesion with the needle is increased. As a result, it may be necessary to acquire a large number of samples, thereby causing pain and discomfort to the patient and increasing a duration of the biopsy procedure. To improve guidance, some biopsy procedures utilize an additional imaging device, such as an ultrasound probe, but such devices can be expensive and can further complicate the biopsy procedure for extracting the sample.

Accordingly, there is a need for additional NM imaging systems, assemblies, and methods of locating lesions within patient tissue and/or extracting samples from the lesions in the patient tissue.

BRIEF DESCRIPTION

In one embodiment, a nuclear medicine (NM) imaging system is provided that includes a gantry and first and second NM cameras coupled to the gantry. The first and second NM cameras have camera surfaces that are configured to face each other while imaging patient tissue therebetween. The NM imaging system also includes an immobilization plate that is configured to be positioned between the first and second NM cameras and extend parallel to the camera surface of the first NM camera. The immobilization plate is movable to and from the camera surface of the first NM camera to compress the patient tissue therebetween, and the second NM camera is movable to and from the immobilization plate. The second NM camera is oriented with respect to a roll axis that extends parallel to the immobilization plate. The second NM camera is rotatable about the roll axis while the immobilization plate and the first NM camera have fixed positions with respect to each other with the patient tissue compressed therebetween.

In another embodiment, a depth detection assembly is provided that includes an elongated tool having a proximal base, a leading end portion, and a central longitudinal axis extending therebetween. The leading end portion is configured to be inserted into patient tissue during a biopsy procedure and advanced toward a lesion in an insertion direction. The depth detection assembly also includes a gamma counter that is coupled to the leading end portion of the elongated tool. The gamma counter includes a detection surface that generally faces in the insertion direction when the elongated tool is inserted into the patient tissue and is configured to detect gamma photons that are incident thereon. The gamma counter is configured to communicate radiation information based on a number of photons detected by the gamma counter.

In yet another embodiment, a method of imaging patient tissue using a nuclear medicine (NM) camera is provided. The method includes holding the patient tissue in a stationary position using an immobilization plate and acquiring a two-dimensional (2D) image of the patient tissue in the stationary position. The 2D image includes a lesion having a 2D location. The method also includes positioning the NM camera relative to the immobilization plate at a lateral position that is based on the 2D location of the lesion. The method also includes rotating the NM camera so that an acute angle is formed between a camera surface of the NM camera and the immobilization plate. The method also includes acquiring a depth-estimating image of the patient tissue in the stationary position while the acute angle exists between the NM camera and the immobilization plate.

DETAILED DESCRIPTION

Figure 1:
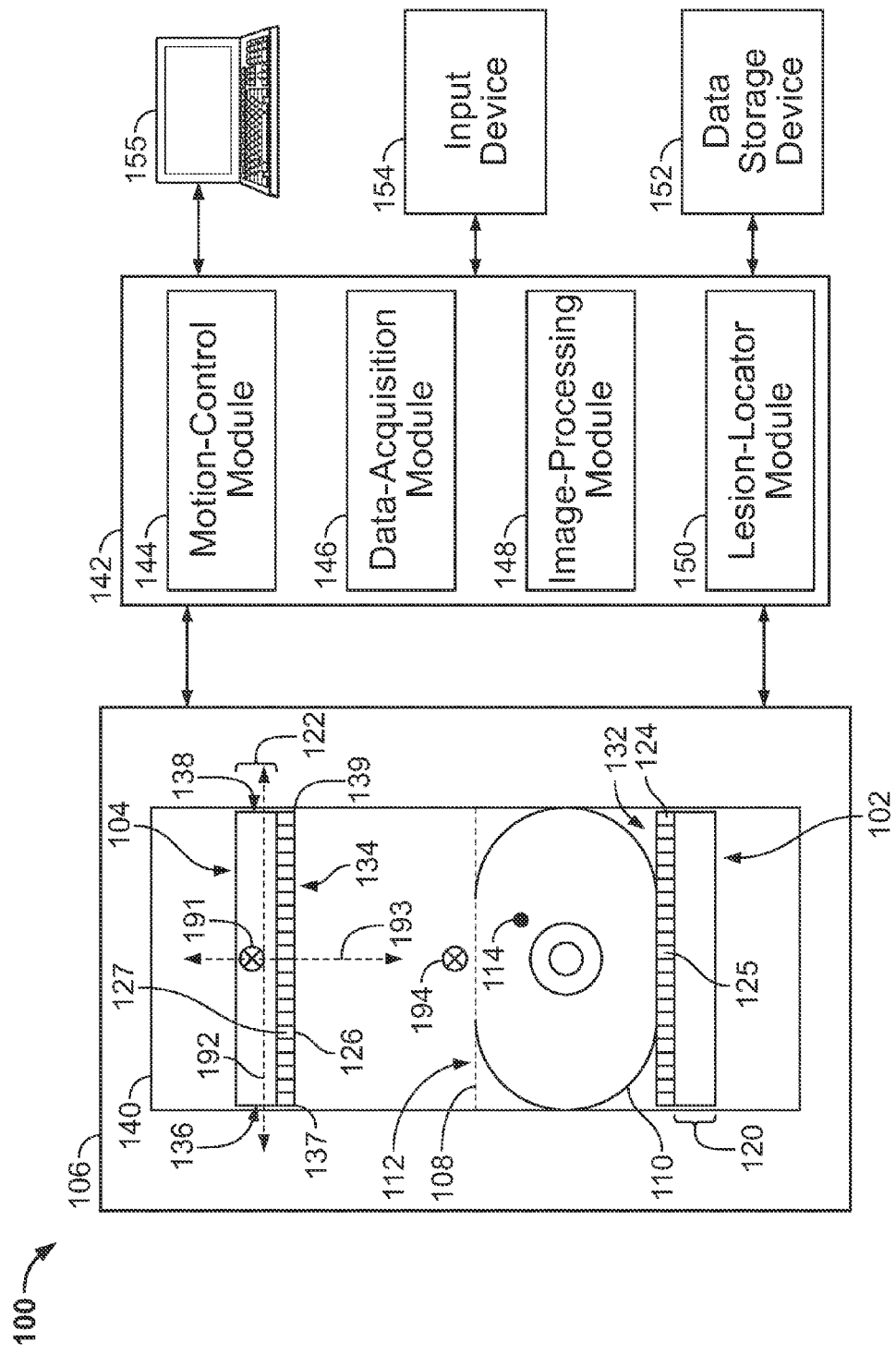
FIG. 1 is a schematic diagram of a nuclear medicine (NM) imaging system in accordance with an embodiment that includes first and second NM cameras and an immobilization plate.

Embodiments described herein include nuclear medicine (NM) imaging systems, depth detection assemblies that may be used with NM imaging systems, and methods relating to the same. The NM imaging systems may include at least one NM camera (or detector head) that is capable of being re-oriented while patient tissue (e.g., breast tissue) is held in a stationary position. In particular embodiments, first and second NM cameras may be provided in which at least one of the first and second NM cameras is capable of being re-positioned with respect to the other. Such embodiments that include movable NM cameras may provide more space for other devices (e.g., biopsy needles, secondary imaging devices, depth detection assemblies, etc.) during an imaging/biopsy session and/or may enable the acquisition of images along different imaging planes to determine a three-dimensional (3D) location of a lesion within a volume of space.

In some embodiments, an immobilization plate may be located between the first and second NM cameras. For example, the immobilization plate and the first NM camera may be positioned relative to each other in order to hold tissue of a patient (hereinafter "patient tissue") between the immobilization plate and the first NM camera. In particular embodiments, the patient tissue is breast tissue and is compressed between the immobilization plate and the first NM camera. The first and second NM cameras may extend parallel to each other such that corresponding camera surfaces of the first and second NM cameras directly face each other.

When the first and second NM cameras face each, a volume of space exists therebetween. During a first image-acquisition stage, at least one of the first and second NM cameras may obtain two-dimensional (2D) images of the volume of space. The first image-acquisition stage is hereinafter referenced as the 2D-acquisition stage and the 2D images are hereinafter referred to as 2D-estimating images. The 2D-estimating images may extend along a first imaging plane. More specifically, while the patient tissue is held in a stationary (or immobilized) position between the immobilization plate and the first NM camera, either or both of the first and second NM cameras may detect radiation from one or more lesions in the patient tissue. By analyzing data from the 2D-estimating images, a 2D location of a lesion within the volume of space may be determined. At least some embodiments set forth herein may execute a second image-acquisition stage, referenced as a depth-estimating stage, to identify a depth of the lesion.

After acquiring the 2D-estimating images, the second NM camera may be configured to move away from the immobilization plate (or the first NM camera) while the patient tissue is held (e.g., compressed) in the stationary position between the immobilization plate and the first NM camera. In some embodiments, the second NM camera is configured to move away from the immobilization plate after acquiring the 2D images and at least one of (a) roll about a first axis (e.g., tilt); (b) pitch about a second axis; or (c) shift laterally in a direction parallel to the immobilization plate. In particular embodiments, the second NM camera may make a combination of the (a), (b), and (c) movements while the patient tissue is in the stationary position. Accordingly, the movability of the second NM camera may allow access to at least one side of the patient tissue so that a depth of the lesion may be determined and/or so that a biopsy device may extract a sample from the patient tissue.

Each lesion has a location within the volume of space that may, for example, be represented by X, Y, Z coordinates. After the first and second NM cameras obtain the 2D-estimating image, a 2D location of one or more lesions may be identified by analyzing the 2D-estimating image. To determine a depth of each lesion, the second NM camera may be moved relative to the immobilization plate while the immobilization plate and the first NM camera have the patient tissue therebetween in the stationary position. For example, the second NM camera may be rolled (or rotated) about the first axis such that the second NM camera forms a non-orthogonal relationship with respect to the immobilization plate (or first NM camera) and, more particularly, forms an acute angle with respect to the immobilization plate. In some cases, the second NM camera may also be shifted laterally in a direction parallel to the immobilization plate. Each lesion may then be detected again by the second NM camera while the second NM camera and the immobilization plate have the non-orthogonal relationship. Using the 2D location and the acute angle formed between the immobilization plate and the second NM camera, the depth of the lesion can be determined. With the location of the lesion within the volume of space known, a biopsy procedure may be performed to extract a sample of the lesion.

In some embodiments, a depth detection assembly or device having an integrated gamma counter may be used to determine the depth of the lesion. In more particular embodiments, the depth detection assembly also includes a biopsy needle. As such, the same device may be used to identify the depth of the lesion and also extract a sample of the lesion. For example, the 2D location of one or more lesions may be identified after the first and second NM cameras obtain the 2D-estimating images. As described herein, the second NM camera may be moved away from the immobilization plate while the patient tissue is held in the stationary position between the immobilization plate and the first NM camera.

A biopsy needle having the integrated gamma counter may be positioned at the 2D location of a lesion and inserted into the patient tissue in a direction toward the lesion. As the biopsy needle approaches the lesion, the gamma counter detects radiation (e.g., gamma photons) emitted from the lesion. A count rate (e.g., number of photons detected within a predetermined period of time) may be a function of a distance between the gamma counter and the lesion. More specifically, the count rate increases as the gamma counter approaches the lesion and decreases after the gamma counter passes the lesion. The depth of the lesion may be associated with a depth of the gamma counter when the count rate has a maximum value. In other words, the radiation may be monitored to identify an inflection in the count rate. The depth at which the inflection occurs may be associated with the depth of the lesion. After determining the depth of the lesion, the biopsy needle may be used to extract the sample of the lesion at the identified depth.

The foregoing and following description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. As used herein, the term "image" broadly refers to both viewable images and data representing a viewable image.

Various embodiments described herein provide systems and methods for locating lesions and/or biopsy guidance in Nuclear Medicine (NM) imaging or, more particularly, Molecular Breast Imaging (MBI). Various embodiments generally include a movable NM camera (or detector head) that (a) provides access to a patient tissue so that a biopsy device may be guided toward the lesion and/or (b) may be used to determine a depth of the lesion. Although the following embodiments are described in the context of MBI, it is understood that such embodiments may also be used in other NM imaging applications in which the patient tissue is not breast tissue.

FIG. 1 is a schematic block diagram of an NM imaging system 100 including a first NM camera 102 and a second NM camera 104 coupled to a gantry 106. At least one of the first and second NM cameras 102, 104 may be movably coupled to the gantry 106. The NM imaging system 100 also includes an immobilization plate 108 coupled to the gantry 106. As used herein, the term "coupled" includes two objects being directly connected to each and two objects being connected through intervening objects. With respect to the NM imaging system 100 in FIG. 1, the first and second NM cameras 102, 104 and the immobilization plate 108 may be supported by the gantry 106 such that an entire weight of each object is held by the gantry 106.

The NM imaging system 100 is configured to detect gamma photons emitted from patient tissue 110, which is hereinafter referred to as a breast 110. The breast 110 may be compressed between the immobilization plate 108 and the first NM camera 102 by moving at least one of the immobilization plate 108 and/or the first NM camera 102 toward the other. The immobilization plate 108 and the first NM camera 102 are configured to have fixed positions with respect to each other so that the breast 110 may be held in a stationary position during an imaging session and a subsequent biopsy procedure. When in the stationary position, the breast 110 is effectively immobilized so that images may be acquired for identifying one or more lesions 114 within the breast 110 and, optionally, a biopsy of each suspicious lesion may be performed using location information based on the images. The breast 110 may be compressed between the immobilization plate 108 and the first NM camera 102.

The immobilization plate 108 may have a fixed position with respect to the breast 110 when images are acquired and/or a biopsy procedure is performed. In some embodiments, the immobilization plate 108 includes an array of passages 112 in which the passages 112 have designated locations within the immobilization plate 108. For example, the passages 112 may be located in a grid-like manner in which the passages 112 have an equal center-to-center spacing between adjacent passages 112. The location of each the passage 112 may correspond to a corresponding 2D location of the volume of space. The passages 112 may be sized and shaped to receive a portion of a biopsy device, such as a biopsy needle. Thus, if the 2D location of a lesion is known, a user may insert an elongated instrument or tool, such as an introducer or biopsy needle, through a corresponding passage 112 that correlates to the known 2D location. As such, the immobilization plate 108 may be used to guide an elongated tool toward a suspected lesion.

The first and second NM cameras 102 and 104 are configured to provide 2D imaging of the breast 110. More specifically, each of the first and second NM cameras 102 and 104 may be capable of capturing a 2D image. In some embodiments, data from each of the 2D images may be combined to construct a single 2D image (e.g., a composite 2D image). The 2D image or images may then be used to obtain a 2D location of the lesion 114 in the breast 110. The 2D location may identify two dimensions or coordinates of the lesion 114, but generally not a third dimension (e.g., depth). A subsequent 2D image may then be used to determine a depth of the lesion 114.

The first and second NM cameras 102, 104 may include respective detectors 120, 122. For instance, the detectors 120, 122 may include scintillation crystal elements, such as cadmium zinc telluride (CdTe or CZT) tiles or like elements. The first and second NM cameras 102, 104 may also include respective collimators 124, 126 that are coupled to the detectors 120, 122, respectively. The collimators 124, 126 are illustrated as thick sheets (e.g., lead) having elongated holes 125, 127, respectively, that extend perpendicular to surfaces of the detectors 122, 124. Each of the holes 125, 127 is configured to only receive gamma photons that are propagating along designated paths that are substantially perpendicular to the surfaces of the detectors 120, 122. If any of the scintillation crystal elements absorb gamma photons, the locations of the excited scintillation elements may be used to determine the 2D location of the lesion.

As shown, the collimators 124, 126 include corresponding camera surfaces 132, 134 of the first and second NM cameras 102 and 104, respectively. Each of the camera surfaces 132, 134 may represent an exterior surface of the corresponding NM camera that is configured to receive the gamma photons emitted from the breast 110. The camera surfaces 132, 134 are planar in the illustrated embodiment.

Although specific configurations of the first and second NM cameras 102, 104 are described herein, it is understood that other types of detectors and collimators may be used. For example, other types of collimators may include diverging, converging, pinhole, cone-beam, fan-beam or slanted holes, among others.

The second NM camera 104 has opposite camera sides 136, 138. The camera sides 136, 138 intersect the camera surface 134 at side edges 137, 139. Although not shown in the cross-section of the second NM camera 104, the second NM camera 104 may have another pair of opposite camera sides having corresponding side edges that intersect the camera surface 134. The side edges 137, 139 and the other pair of side edges (not shown) may define a perimeter of the camera surface 134.

The second NM camera 104 may be configured to move with respect to the breast 110 when the breast 110 is held in a stationary position. For example, the second NM camera 104 may be configured to move with respect to the immobilization plate 108 when the immobilization plate 108 and the first NM camera 102 have the breast 110 held in a stationary position. The second NM camera 104 is oriented with respect to a roll axis (or first axis) 191 that extends into and out of the page of FIG. 1, a pitch axis (or second axis) 192 that extends laterally or horizontally along the page, and a yaw axis (or third axis) 193 that extends vertically along the page. Although orientation terms such as horizontal, vertical, and the like may be used herein, such terms are not intended to require a certain orientation or position with respect to gravity. For example, depending on the position of the second NM camera 104, the yaw axis 193 or the pitch axis 192 may extend parallel to the direction of gravitational pull.

In some embodiments, the second NM camera 104 is configured to move to and from the immobilization plate 108 (or the first NM camera 102) along the yaw axis 193. For instance, after 2D-estimating images of the breast 110 are acquired, the second NM camera 104 may be moved (e.g., along a designated path) away from the immobilization plate 108. In certain embodiments, the second NM camera 104 may also be configured to at least one of (a) rotate (e.g., tilt or swivel) about the roll axis 191 in either a clockwise or counter-clockwise manner; (b) rotate about the pitch axis 192 in either a clockwise or counter-clockwise manner; or (c) shift or slide laterally in a direction that is parallel to the immobilization plate 108. As such, the second NM camera 104 may be moved to allow access to the immobilization plate 108 so that another device, such as a biopsy device and/or depth detection assembly, may be positioned along the immobilization plate 108. In some cases, the second NM camera 104 may be moved so that either of the side edges 137, 139 may be positioned adjacent to the immobilization plate 108. In such embodiments, the second NM camera 104 may have a non-orthogonal relationship with respect to the immobilization plate 108. The second NM camera 104 may then be used to acquire a depth-estimating image of the breast 110 and determine a depth of the lesion 114 within the breast 110.

In the illustrated embodiment, each of the first and second NM cameras 102, 104 is coupled to a movable base 140. The movable base 140 may be rotatable about a system axis 194 that may extend parallel to or coincide with the roll axis 191. When the movable base 140 is rotated about the system axis 194 in either of a clockwise or counter-clockwise manner, the first and second NM cameras 102, 104 may move with the movable base 140.

The NM imaging system 100 also includes a computing system 142 that is communicatively coupled to at least one of the first and second NM cameras 102, 104, the immobilization plate 108, and the movable base 140. The computing system 142 has one or more circuit modules for controlling movement of the various components, imaging the patient tissue, analyzing image data to locate one or more lesions 114, and/or guiding a biopsy device to extract sample(s) of the lesion(s) 114. The computing system 142 may include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

The block diagrams provided herein, such as in FIG. 1, illustrate various blocks labeled "module." It is to be understood that the modules may represent circuit modules that may be implemented as hardware with associated instructions (e.g., software stored on a tangible and non-transitory computer readable storage medium, such as a computer hard drive, ROM, RAM, or the like) that perform the operations described herein. The hardware may include state machine circuitry that is hard-wired to perform the functions described herein. Optionally, the hardware may include electronic circuits that include and/or are connected to one or more logic-based devices, such as microprocessors, processors, controllers, or the like. Optionally, the modules may represent processing circuitry such as one or more field programmable gate array (FPGA), application specific integrated circuit (ASIC), or microprocessor. The circuit modules in various embodiments may be configured to execute one or more algorithms to perform functions described herein. The one or more algorithms may include aspects of embodiments disclosed herein, whether or not expressly identified in a flowchart or a method.

By way of example, the computing system 142 may include a motion-control module 144. The motion-control module 144 may be operably coupled to one or more of the movable base 140, the first and second NM cameras 102, 104, and/or the immobilization plate 108. The motion-control module 144 may generate commands for automatically controlling movement of a component. For example, the motion-control module 144 may be configured to command a motor (not shown) for rotating the movable base 140 about the system axis 194. The motion-control module 144 may receive position data regarding a position (e.g., orientation and/or spatial location) of the component(s). The position data may be communicated from a sensor of the corresponding component to the motion-control module 144. For example, the movable base 140 and/or the first and second NM cameras 102, 104 may include corresponding orientation sensors (e.g., accelerometers, rotary encoders).

The position data may represent a degree, such as between 0° and 359°. The immobilization plate 108 and/or the first and second NM cameras 102, 104 may include a corresponding position sensor (e.g., linear encoder, proximity sensor) that measures a distance between two objects and/or confirms whether two objects are immediately adjacent to or abutting each other. The position data may represent a designated distance (e.g., centimeters or millimeters) between the two objects or may represent information that confirms one object is immediately adjacent to another object.

By way of example, the second NM camera 104 may include an accelerometer, a rotary encoder, and first and second linear encoders that each communicate position data to the motion-control module 144. The position data from the accelerometer may represent an orientation of the second NM camera 104 relative to gravity. The rotary encoder may be coupled to a rotary motor that controls movement of the second NM camera 104. The position data from the rotary encoder may represent a rotational degree (e.g., between 0° and 180°) of the rotary motor with respect to the roll axis 191. The motion-control module 144 may determine a rotational orientation of the second NM camera 104 using the position data from the accelerometer and the rotary encoder. A first linear encoder may measure a distance between a designated point of the second NM camera 104 (e.g., a center of the camera surface 134) and a designated point of the immobilization plate 108 or the first NM camera 102. The motion-control module 144 may determine an elevation position of the second NM camera 104 using the position data. A second linear encoder may measure a lateral location of the second NM camera 104 along the pitch axis 192. The motion-control module 144 may determine a lateral position of the second NM camera 104 using the position data. In certain embodiments, the rotational orientation is with respect to the roll axis 191, the elevation position is with respect to the yaw axis 193, and the lateral position is with respect to the pitch axis 192.

It is understood that the above methods of determining the designated position (e.g., the rotational orientation, the elevation position, and the lateral position) of the second NM camera 104 is illustrative only and that there may be alternative methods of determining the designated position of the second NM camera 104.

The motion-control module 144 may automatically move one or more components into designated positions, may receive commands from a user for moving the one or more components into designated positions, may determine a designated position of the one or more components after a user has manually positioned the component(s), or a combination thereof. For instance, the motion-control module 144 may command one or more motors (not shown) for moving one or more of the components into the designated positions. As a specific example, the motion-control module 144 may automatically command one or more motors to move the second NM camera 104 to a designated position. The designated position may have a designated location along the yaw axis 193, a designated location along the pitch axis 192, and a rotational orientation with respect to the roll axis 191. In some embodiments, the motion-control module 144 may automatically control the first and second NM cameras 102, 104 to move into designated positions for a 2D-acquisition stage and then automatically control the second NM camera 104 to move into a designated position for a subsequent depth-acquisition stage. The designated position of the second NM camera 104 during the depth-acquisition stage may be based on a 2D location of lesion that has been identified in the 2D-estimating images.

The positions of the various components, including absolute and relative positions, may be recorded or stored by the motion-control module 144 for further processing by the computing system 142. By way of example, the motion-control module 144 may record a separation distance between the first and second NM cameras 102, 104 at a 2D-acquisition stage, rotational orientations of the first or second NM cameras 102, 104 (e.g., between 0° and 180°) with respect to a designated axis, or a rotational orientation of the movable base 140 (e.g., between 0° and 359°) with respect to the system axis 194.

The NM imaging system 100 may also include a data-acquisition module 146 that receives analog and/or digital electrical signal data produced by the NM cameras 102, 104 and decodes the signal data for subsequent processing. For example, the NM imaging system 100 may also include an image-processing module 148 that is configured to generate images based on the signal data. The images may include viewable images or image data that is not presently viewed. The images may include, for example, 2D images acquired when the first and second NM cameras 102, 104 directly face each other or depth-estimating images that are acquired when the second NM camera 104 has a non-orthogonal relationship with respect to the immobilization plate 108 or the first NM camera 102.

The NM imaging system 100 also includes a lesion-locator module 150 configured to perform one or more location determination methods, for example, to determine a 2D location, a depth, and/or a 3D location of the lesion 114 in the breast 110. In addition to the above components, the NM imaging system 100 may include a data storage device 152 for storing data from the motion-control module 144, the data-acquisition module 146, the image-processing module 148, and/or the lesion-locator module 150. The NM imaging system 100 may also include an input device 154 (e.g., keyboard, mouse, buttons, knobs, and the like) to receive user inputs and a display 155 to display images. In some embodiments, the input device 154 is part of the display 155. For example, the input device 154 and the display 155 may be provided by a single touchscreen or a personal communication device.

With respect to the various embodiments described herein, it should be noted that the particular arrangement of components (e.g., the number, types, placement, or the like) may be modified in various alternate embodiments. For instance, different numbers of a given module, device, or assembly may be employed or a different type or types of a given module, device, or assembly may be employed. Moreover, a given module, device, or assembly may be added or omitted in some alternate embodiments. It is also understood that the various modules described herein may be part of a common processing unit (e.g., microprocessor) or distributed across multiple processing units.

Figure 2:
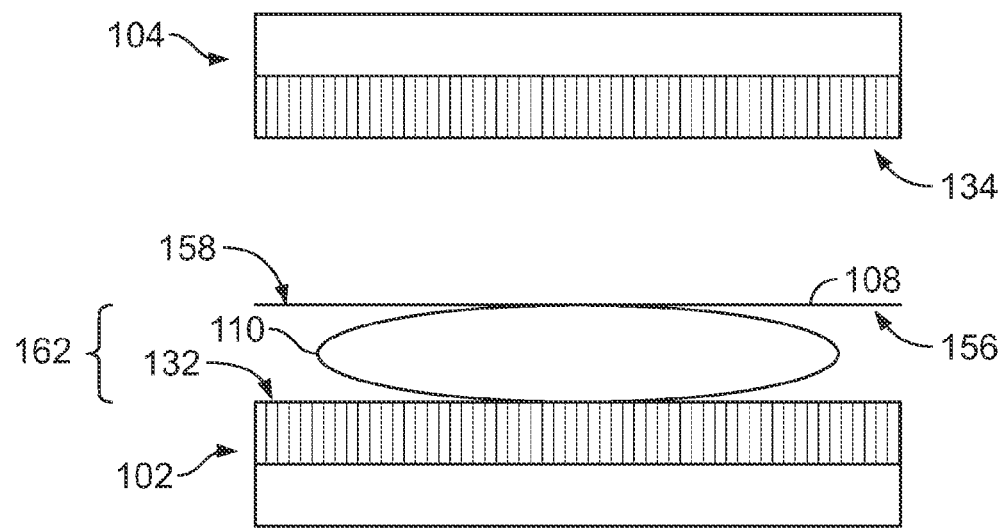
FIG. 2 is a schematic diagram illustrating the first and second NM cameras and the immobilization plate during a patient-positioning stage.

FIG. 2 is a schematic view of the first and second NM cameras 102, 104 during a patient-positioning stage. During the patient-positioning stage, the breast 110 may be positioned between the first NM camera 102 and the immobilization plate 108 with the immobilization plate 108 located to compress and hold the breast 110 therebetween. The immobilization plate 108 has opposite first and second plate sides 156, 158. The first plate side 156 faces the camera surface 132 of the first NM camera 102, and the second plate side 158 faces the camera surface 134 of the second NM camera 104.

As shown in FIG. 2, a separation distance or spacing 162 exists between the first NM camera 102 and first plate side 156 of the immobilization plate 108. The separation distance 162 may be changed to accommodate breasts with different sizes or densities. The separation distance 162 between the camera surface 132 and the first plate side 156 may be registered automatically or manually. For example, the separation distance 162 may represent a maximum depth for a lesion location during subsequent analysis. Accordingly, the first NM camera 102 and the immobilization plate 108 may apply an immobilizing force to compress the breast 110. The compression may be measured by, for example, a sensor that is coupled to the immobilization plate 108 and/or the first NM camera 102. The compression may be less than the pressure applied during an x-ray mammography exam, but sufficient for immobilizing the breast 110 for the duration of the different imaging acquisitions and optional biopsy procedure. It should be noted that the immobilization and/or compression of the breast 110 shown in the various figures may be exaggerated for illustration.

Figure 3:
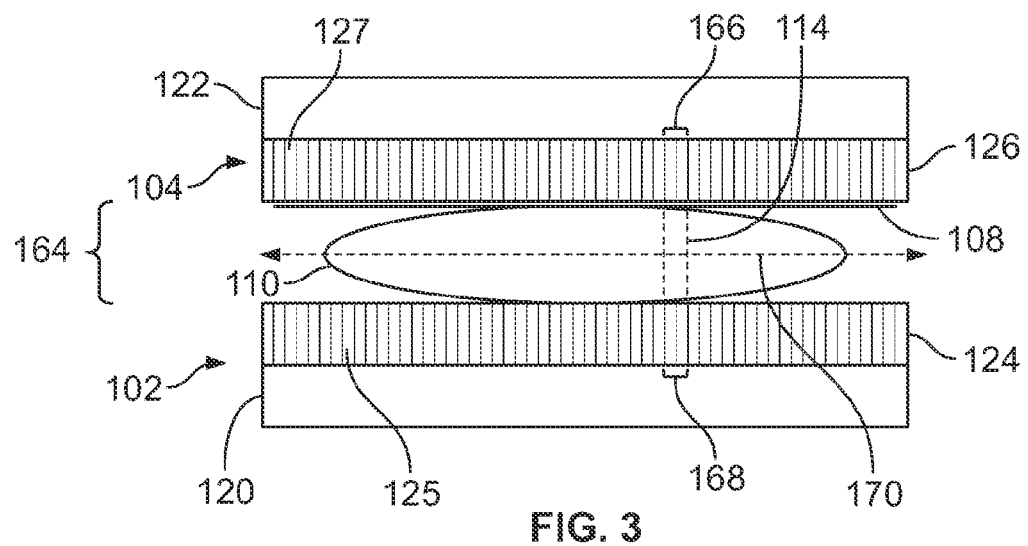
FIG. 3 is a schematic diagram illustrating the first and second NM cameras and the immobilization plate during a two-dimensional (2D) image-acquisition stage.

FIG. 3 is a schematic view of the first and second NM cameras 102, 104 during a 2D-acquisition stage. Once the breast 110 is immobilized between the first NM camera 102 and the immobilization plate 108, the second NM camera 104 may be moved (e.g., translated) toward the immobilization plate 108 and positioned such that the camera surface 134 (FIG. 2) of the second NM camera 104 interfaces with the second plate side 158 (FIG. 2). For example, the camera surface 134 of the second NM camera 104 may directly abut or may be slightly spaced apart from the second plate side 158. The motion-control module 144 may automatically detect or receive user inputs regarding a separation distance or spacing 164 between the camera surfaces 132, 134 of the first and second NM cameras 102, 104, respectively, which may be substantially equal to the separation distance 162 between the first plate side 156 and the camera surface 132.

During the 2D-acquisition stage, one or more 2D-estimating images may be acquired by the first NM camera 102 and/or the second NM camera 104. The detector 120 and/or the detector 122 may detect gamma photons from the breast 110 and communicate such data to the computing system 142 (FIG. 1) for processing. Using the illustrated embodiment of FIG. 3 as an example, the breast 110 may include the lesion 114, which has absorbed a radiopharmaceutical (e.g., Tc-99m sestamibi or other agent). As described herein for some embodiments, each of the holes of the collimators 124, 126 may receive designated gamma photons that propagate perpendicular to the camera surfaces 132, 134 (FIG. 2), respectively, and permit such gamma photons to be incident on detection surfaces of the detectors 120, 122. In the illustrated example, the scintillation crystal elements along an area 166 of the detection surface of the detector 120 and the scintillation crystal elements along an area 168 of the detection surface of the detector 122 may be excited by gamma photons. The areas 166, 168 may correspond to the 2D location of the lesion 114. The image-processing module 148 may process the data to generate 2D-estimating images that are capable of being viewed on the display 155 and/or process the 2D-estimating images to identify the 2D location of the lesion 114. The lesion 114 is represented as a dashed column in FIG. 3, because the depth of the lesion 114 has not yet been determined.

As shown in FIG. 3, the 2D-estimating images may be acquired along an imaging plane 170 that extends parallel to the immobilization plate 108. The imaging plane 170 extends perpendicular to the respective holes 125, 127 of the collimators 124, 126. Although the imaging plane 170 appears to bisect the breast 110 in FIG. 3, it is understood that the entire breast 110 is captured in the 2D-estimating images. The imaging plane 170 is only shown in FIG. 3 to illustrate an orientation of the field of view provided by the 2D-estimating images.

After acquiring the 2D-estimating image(s), the lesion-locator module 150 may determine a 2D location of one or more of the lesions in each of the 2D-estimating images. For example, the lesion-locator module 150 may analyze the 2D-estimating image to identify pixels having intensities that exceed a designated value. The lesion-locator module 150 may use one or more image processing algorithms, such as full-width half maximum (FWHM), to identify the pixels. After identifying the pixels that exceed a designated value, the lesion-locator module 150 may analyze the pixels and identify clusters of pixels. Each cluster of pixels in the 2D-estimating image may correspond to a lesion within the breast.

In some embodiments, the lesion-locator module 150 may analyze each cluster of pixels to determine a center of the corresponding lesion. The 2D location of the center in the 2D-estimating image may be designated as the 2D location of the lesion. For example, the center may be a geometric center of the cluster of pixels in the 2D-estimating image. Alternatively, the center may be a weighted center that is based, in part, on an intensity of each pixel within the cluster. The center may be a single pixel in the 2D-estimating image or an area defined by a plurality of pixels in the 2D-estimating image. In some embodiments, the lesion-locator module 150 may analyze each cluster in the 2D-estimating image to determine a perimeter of the lesion within the 2D-estimating image that, in turn, may define the 2D location of the lesion. The perimeter may be defined by coordinates (e.g., X, Y coordinates). For example, for each X value within a designated range, there may be a range of Y values or vice versa. However, it is noted that above is exemplary only and is not intended to be exhaustive. Alternative methods may be used for identifying lesions within a 2D-estimating image and designating a 2D location of the lesion within the 2D-estimating image.

Figure 4:
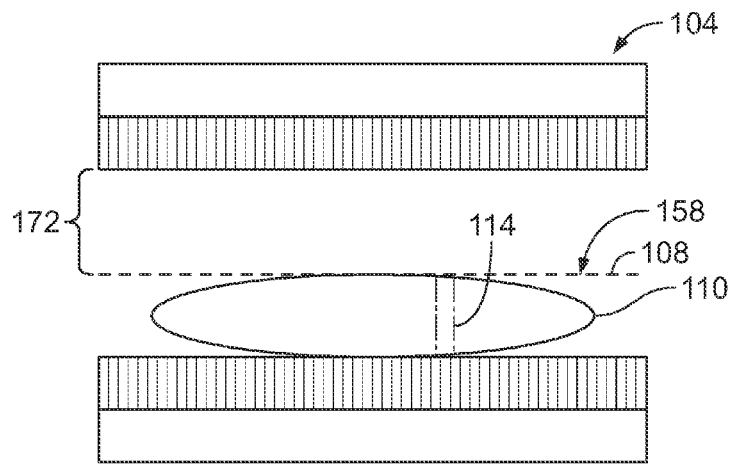
FIG. 4 is a schematic diagram illustrating movement of the second NM camera away from the immobilization plate.
Figure 5:
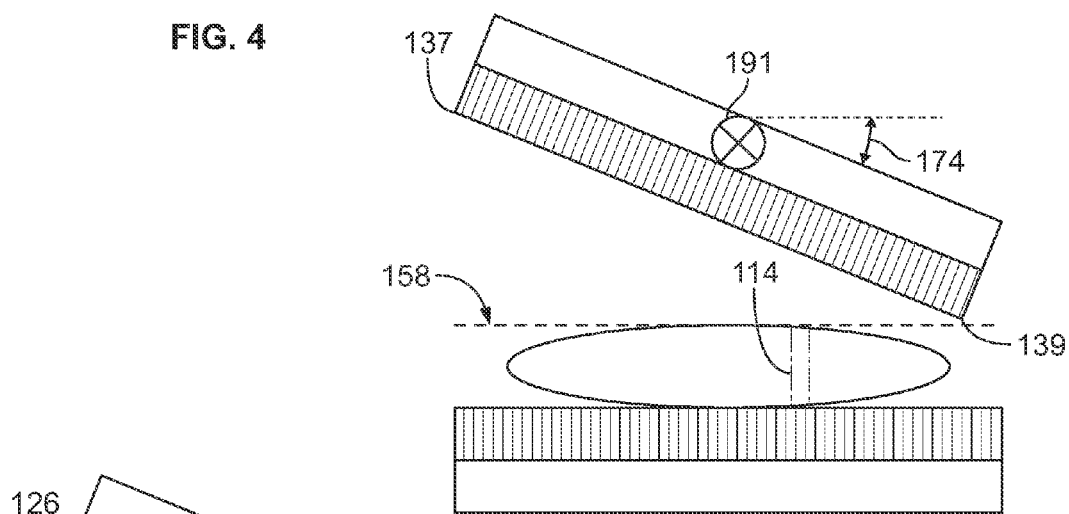
FIG. 5 is a schematic diagram illustrating rotational movement of the second NM camera with respect to the immobilization plate.
Figure 6:
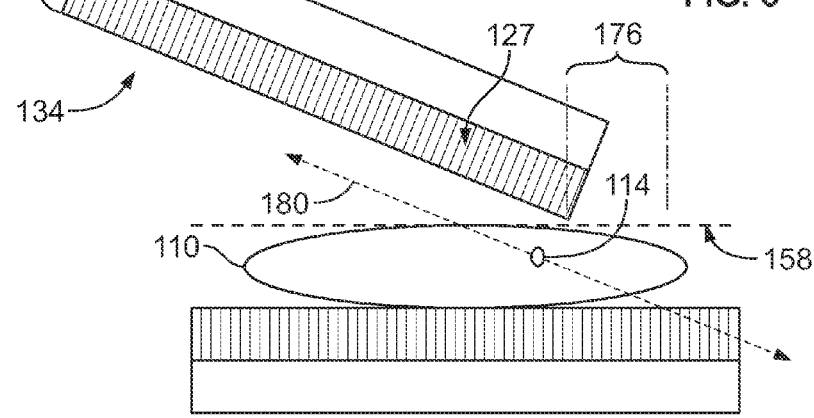
FIG. 6 is a schematic diagram illustrating lateral movement of the second NM camera with respect to the immobilization plate.

FIGS. 4-6 are schematic side views that illustrate the different movements that the second NM camera 104 may make to position the second NM camera 104 relative to the lesion 114. Collectively, the movements may place the second NM camera 104 in a designated position for acquiring a depth-estimating image. Alternatively or in addition to, the collective movements may place the second NM camera 104 in a designated position to provide space along the second plate side 158 of the immobilization plate 108 so that other devices may be positioned therealong. The designated position (shown in FIG. 6) may include a lateral position of the second NM camera 104, an elevation position of the second NM camera 104, and a rotational orientation of the second NM camera 104. The designated position of the second NM camera 104 may be determined, at least in part, by the 2D location of the lesion 114.

Although FIGS. 4-6 indicate that the second NM camera 104 is moved vertically, rotationally, and horizontally at separate times, it is understood that one or more of the movements may be performed concurrently. For example, the second NM camera 104 may be moved, simultaneously, away from the immobilization plate 108 and along the immobilization plate 108 such that the second NM camera 104 effectively moves in a non-orthogonal direction with respect to the immobilization plate 108. Likewise, the second NM camera 104 may be rotated while the second NM camera 104 is moved vertically and/or laterally with respect to the immobilization plate 108.

FIG. 4 shows the second NM camera 104 relative to the immobilization plate 108 after the second NM camera 104 has been moved away from the immobilization plate 108 by an elevation distance 172 (e.g., 40 mm) in a direction that is perpendicular to the immobilization plate 108. The elevation distance 172 may be based on the 2D location of the lesion 114. In certain embodiments, the movement away from the immobilization plate 108 occurs while the breast 110 is in the stationary position.

FIG. 5 shows the second NM camera 104 relative to the immobilization plate 108 after the second NM camera 104 has been rotated about the roll axis 191 by a roll angle 174 (e.g., 35°). The roll angle 174 may be based on the 2D location of the lesion 114. After rotating the second NM camera 104, the side edge 139 is immediately adjacent to the immobilization plate 108 and the side edge 137 is spaced apart from the immobilization plate 108. In some cases, the side edge 139 may directly engage the second plate side 158 of the immobilization plate 108 or have a small nominal gap therebetween.

FIG. 6 shows the second NM camera 104 relative to the immobilization plate 108 after the second NM camera 104 has been moved laterally in a direction parallel to the immobilization plate 108 by a lateral distance 176 (e.g., 10 mm). In particular, the side edge 139 has moved the lateral distance 176 along the second plate side 158 of the immobilization plate 108. The lateral distance 176 may be based on the 2D location of the lesion 114. The elevation distance 172, the roll angle 174, and the lateral distance 176 may be determined by the motion-control module 144 and detected by the sensors described above (e.g., accelerometers, encoders, and the like) to confirm that the second NM camera 104 is in the designated position.

FIG. 6 shows the second NM camera 104 in the designated position for acquiring the depth-estimating image. As described above, the elevation distance 172 (FIG. 4), the roll angle 174 (FIG. 5), and the lateral distance 176 may be based on the 2D location of the lesion 114. The designated position is configured so that the second NM camera 104 may acquire the depth-estimating image of the breast 110, including the lesion 114, along an imaging plane 180. The depth-estimating image is also a 2D image, but the imaging plane 180 is non-orthogonal with respect to the imaging plane 170 (FIG. 3). Similar to the imaging plane 170, the imaging plane 180 extends perpendicular to the holes 127 of the collimator 126. Based on the orientation of the imaging plane 180 relative to the breast 110, a portion of the breast 110 may have a higher resolution than other portions of the breast. More specifically, the portion of the breast 110 that is closer to the camera surface 134 may have a higher resolution than portions of the breast 110 that are further away. As described below, by acquiring the depth-estimating image that is non-orthogonal with respect to the 2D-estimating image, the depth-estimating image and the 2D-estimating image may then be analyzed to determine a depth of the lesion 114.

Figure 7:
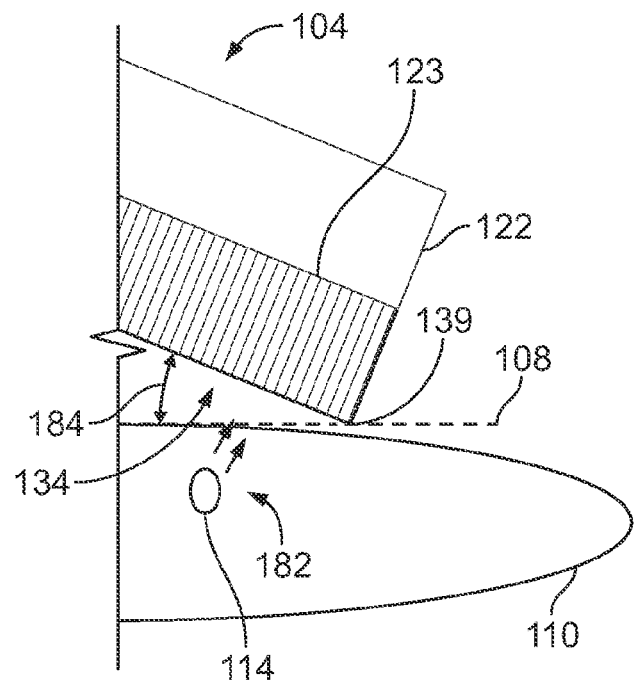
FIG. 7 is a schematic diagram illustrating a relative position between the second NM camera and a lesion during a depth-determining stage.
Figure 8:
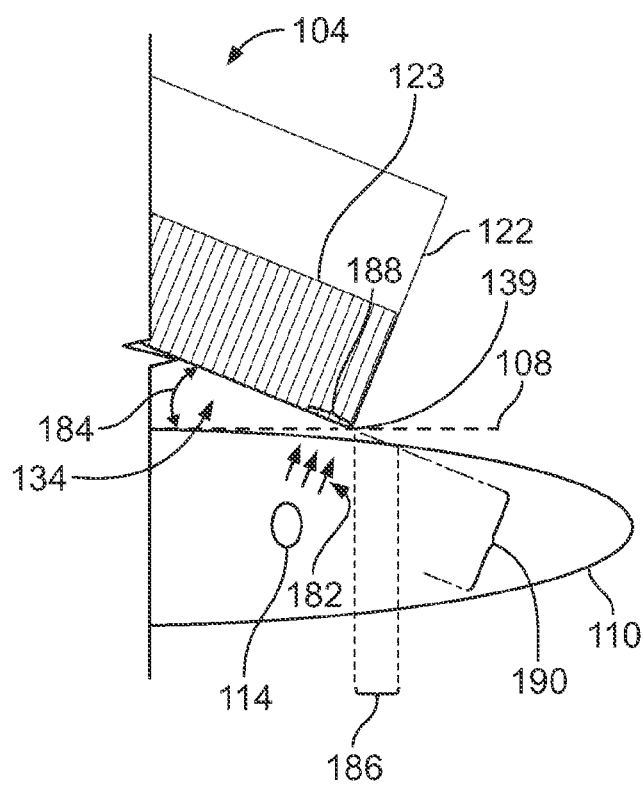
FIG. 8 is a schematic diagram illustrating another relative position between the second NM camera and the lesion during the depth-determining stage.

FIGS. 7 and 8 show enlarged schematic views of the second NM camera 104 relative to the immobilization plate 108 and the breast 110. When the second NM camera 104 has a non-orthogonal relationship with respect to the immobilization plate 108, an acute angle 184 may exist between the camera surface 134 of the second NM camera 104 and the immobilization plate 108. In FIGS. 7 and 8, the acute angle 184 is about 35°. The acute angle 184 may have other values, such as between about 5° and about 85°. As shown, the detector 122 includes a detection surface 123 having elements that are configured to detect gamma photons (indicated by arrows 182). For example, the elements may be cadmium zinc telluride (CZT) tiles. In the illustrated embodiment, the detection surface 123 also forms the acute angle 184 with respect to the immobilization plate 108.

Embodiments set forth herein may be configured to adjust a lateral position of the second NM camera 104 so that a higher resolution of the lesion 114 is obtained in the depth-estimating image. Because the depth of the lesion 114 may not be known when the second NM camera 104 and the immobilization plate 108 have the non-orthogonal relationship, the second NM camera 104 may be configured to scan the breast 110 along a lateral distance 186 (FIG. 8) to identify a depth-estimating image that has a higher resolution.

For instance, the NM imaging system 100 (FIG. 1) may adjust the lateral position of the second NM camera 104 so that a working distance 190 between the lesion 114 and a designated area 188 of the camera surface 134 that receives the gamma photons 182 is reduced. By way of one example, the second NM camera 104 in FIG. 7 is offset with respect to the NM camera 104 in FIG. 8 by a lateral distance 186. By moving the second NM camera 104 the lateral distance 186, the working distance 190 is reduced. As the working distance 190 reduces, a resolution of the lesion 114 within the depth-estimating images may increase because more gamma photons 182 may be incident on the detection surface 123. In other embodiments, the working distance 190 may also be measured between an area of the detection surface 123 that detects the gamma photons 182 and the lesion 114.

In particular embodiments, the designated area 188 is proximate to the side edge 139 of the second NM camera 104. For example, the designated area 188 may include or be adjacent to the side edge 139. In some embodiments, the designated area 188 may be located within ⅓ of the camera surface 134 that includes the side edge 139. In more particular embodiments, the designated area 188 may be located in ⅕ of the camera surface 134 that includes the side edge 139.

When the second NM camera 104 is initially positioned while having the non-orthogonal relationship with respect to the immobilization plate 108, the second NM camera 104 may have a lateral position that enables the detection surface 123 to capture a bottom of the breast 110, which is the portion of the breast 110 that is in contact with the first NM camera 102 (FIG. 1). The initial lateral position is based on the 2D location of the lesion 114 and the acute angle 184. As the second NM camera 104 acquires multiple depth-estimating images of the breast 100 at different lateral positions, the lesion-locator module 150 may compare each depth-estimating image to identify the depth-estimating image with the highest resolution of the lesion 114.

Figures 9, 10:
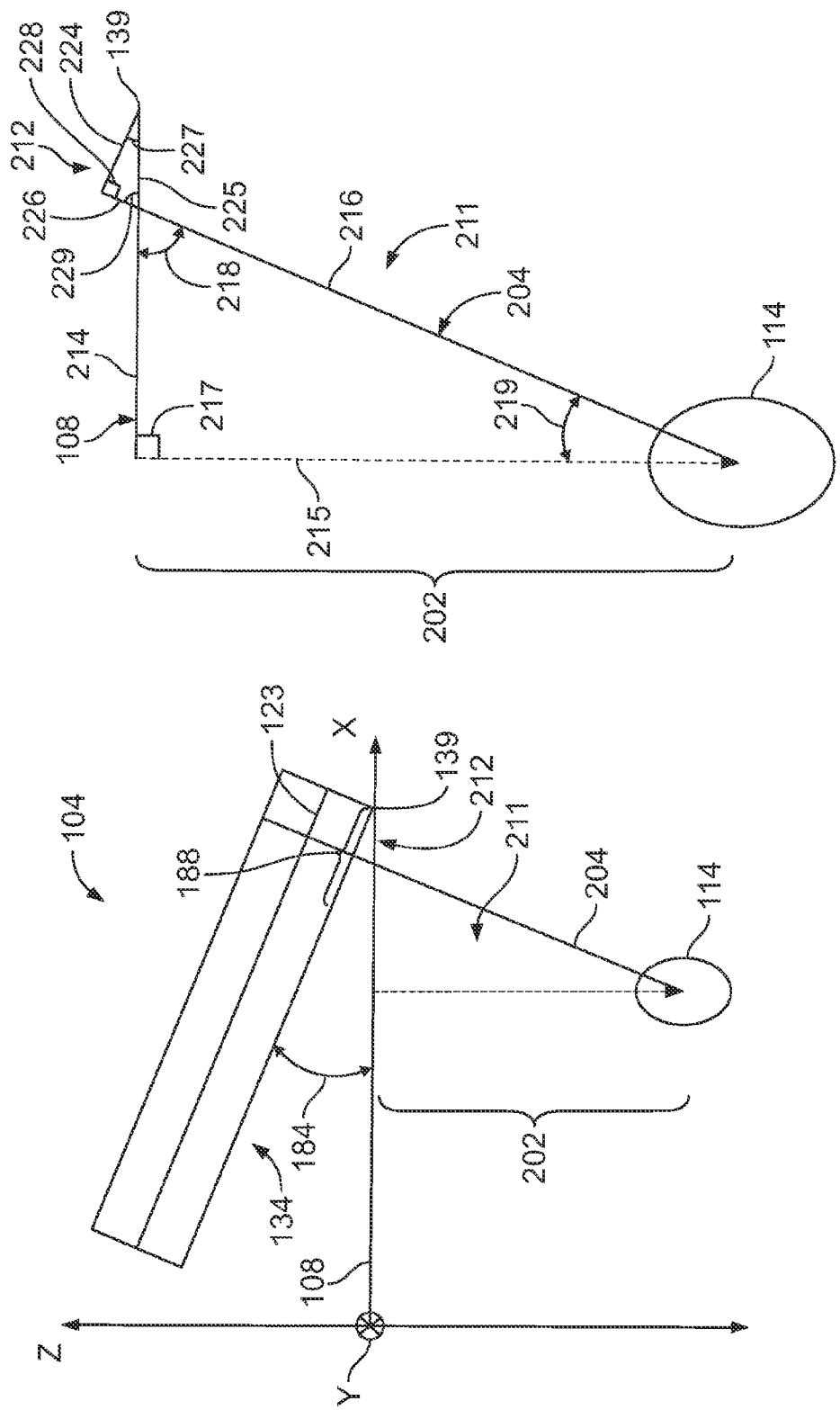
FIG. 9 illustrates a geometric relationship between the second NM camera and the lesion during the depth-determining stage.
FIG. 10 illustrates the geometric relationship in greater detail.

FIG. 9 provides a geometric representation of the second NM camera 104 relative to the lesion 114 and the immobilization plate 108. Mutually perpendicular axes are also shown in FIG. 9, which are labeled as X, Y, and Z axes. The immobilization plate 108 coincides with the X axis. For illustrative purposes, the various distances between the different elements have been increased.

After positioning the second NM camera 104 in the designated position, the acute angle 184 is known. For example, the acute angle 184 may be communicated to the motion-control module 144 and/or the lesion-locator module 150 (both shown in FIG. 1) by a rotary encoder. As shown, a line 204 that extends perpendicular to the camera surface 134 (or the detection surface 123) may intersect the lesion 114, the camera surface 134, and the detection surface 123. The position of the line 204 is based on a 2D location of the lesion 114 in the depth-estimating image and may represent the approximate path taken by gamma photons from the lesion 114. More specifically, the depth-estimating image may include a cluster of pixels that correspond to the lesion 114. The line 204 may project through a center of an area of the detection surface 123 that detected the gamma photons. Because the detection surface 123 and the camera surface 134 are parallel and the line 204 is perpendicular to each, the line 204 also projects through a center of the designated area 188 along the camera surface 134. In a similar manner as described above with respect to the 2D location of the lesion 114 in the 2D-estimating image, a 2D location along the camera surface 134 may be assigned that corresponds to the lesion 114 in the depth-estimating image. As shown, the line 204 creates primary and secondary triangles 211, 212 with the X axis and the camera surface 134.

FIG. 10 illustrates an isolated view of the primary and secondary triangles 211, 212. The primary triangle 211 includes legs 214, 215, and 216 and angles 217, 218, 219. The secondary triangle 212 includes legs 224, 225, and 226 and angles 227, 228, 229. As shown, the depth 202 corresponds to a length of the leg 215. The depth 202 may be determined by using trigonometric formulas. For example, a length of the leg 224 of the secondary triangle 212 may be determined based on a 2D location of a center of the lesion 114 in the depth-estimating image. The angle 227 is equal to the acute angle 184 (FIG. 9). The angle 228 of the secondary triangle 212 is 90° because the line 204 is perpendicular to the camera surface 134 (FIG. 9). Because a sum of the three angles in a triangle must equal 180°, the angle 229 of the secondary triangle 212 may be calculated. Based on geometric rules, the angle 229 is equal to the angle 218 of the primary triangle 211 and the angle 217 of the primary triangle 211 is equal to 90°. Consequently, the angle 219 may be calculated and, in this example, is equal to the acute angle 184.

The side edge 139, which is the point at which the legs 224 and 225 intersect, may have a 2D location along the immobilization plate 108. The 2D location of the side edge 139 may be determined by the motion-control module 144. Because the angles 227-229 are known and the length of the leg 224 is known, a length of the leg 225 may be calculated. A length of the leg 214 may then be determined based on the length of the leg 225 and the 2D locations of the side edge 139 and the lesion 114. With the length of the leg 214 and the angles 217-219 known, the length of the leg 215 and, hence, the depth 202 of the lesion 114 may be calculated using trigonometric formulas. Accordingly, the 2D location of the lesion 114 and the acute angle 184 formed between the camera surface 134 and the immobilization plate 108 when the depth-estimating image is acquired may be used to determine the depth 202 of the lesion 114.

It is noted that the above trigonometric calculation of the depth 202 is just one example of estimating the depth 202 and is not intended to be limiting. Other calculations may be made to estimate the depth 202.

Accordingly, embodiments may analyze a 2D image (i.e., the 2D-estimating image) taken along a first imaging plane to determine a 2D location of a lesion in a patient tissue and then analyze another 2D image (i.e., the depth-estimating image) taken along a non-orthogonal second imaging plane to determine a depth of the lesion. As such, a 3D location of the lesion within the patient tissue may be determined. After determining the 3D location of the lesion, a biopsy procedure may be performed by directing a biopsy needle toward the lesion based on the 3D location.

Figure 11:
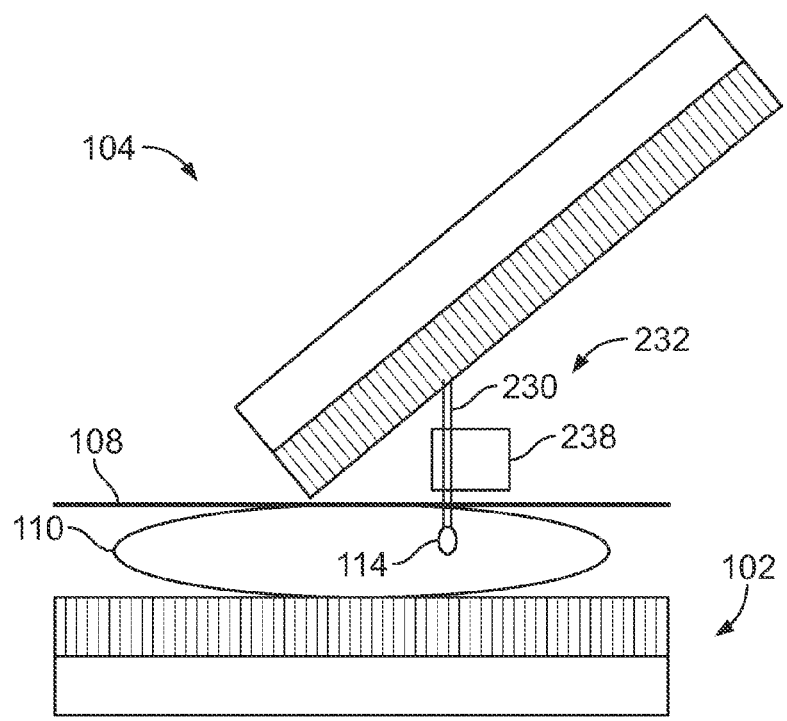
FIG. 11 is a schematic diagram illustrating the first and second NM cameras and the immobilization plate of FIG. 1 during a biopsy-guidance stage.
Figure 12:
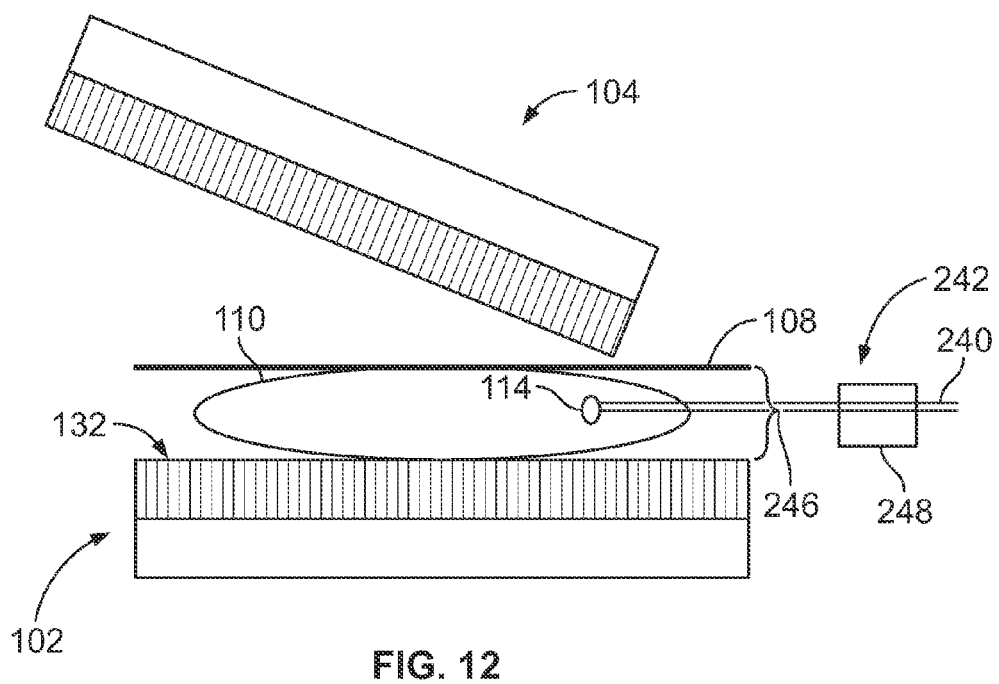
FIG. 12 is a schematic diagram illustrating the first and second NM cameras and the immobilization plate of FIG. 1 during another biopsy-guidance stage.

FIGS. 11 and 12 are schematic side views of the first and second NM cameras 102, 104 relative to the immobilization plate 108 and the breast 110 during a corresponding biopsy procedure. FIG. 11 illustrates a vertical biopsy procedure in with an elongated tool 230 of a biopsy device 232 is inserted through a corresponding passage 112 (FIG. 1) of the immobilization plate 108 in a direction that is perpendicular to the immobilization plate 108. The elongated tool 230 may be at least one of an introducer, biopsy needle, guidewire, or the like. The passage 112 may be determined by the 2D location of the lesion 114. The biopsy device 232 may also include a device base 238 for supporting the elongated tool 230 and controlling the insertion process (e.g., speed, depth) of the elongated tool 230 or the biopsy process. For example, the device base 238 may include a vacuum device for extracting a sample.

FIG. 12 illustrates a biopsy procedure in which an elongated tool 240 (e.g., introducer, biopsy needle, and/or guidewire) of a biopsy device 242 is inserted in a direction that is parallel to the immobilization plate 108. The elongated tool 240 is inserted through a gap or spacing 246 between the immobilization plate 108 and the camera surface 132 of the first NM camera 102 and into the breast 110. The biopsy device 242 may also include a device base 248 similar to the device base 238.

A healthcare provider or other qualified individual may determine whether to perform the vertical biopsy procedure (FIG. 11) or the lateral biopsy procedure (FIG. 12) based on the 3D location of the lesion 114. In other embodiments, the NM imaging system 100 (FIG. 1) may automatically suggest or recommend the biopsy procedure to the healthcare provider based on the 3D location. The type of biopsy procedure to perform may be determined by a shortest path through the breast 110 to the lesion 114 in order to reduce damage to the breast 110. By way of example, the NM imaging system 100 may identify the passage 112 (FIG. 1) that the elongated tool 230 should be inserted through and communicate the passage identity to the healthcare provider. In some embodiments, the NM imaging system 100 may automatically perform the biopsy procedure.

In either of the lateral or vertical biopsy procedures, the second NM camera 104 may be positioned to image the elongated tool of the corresponding biopsy device. Images from the second NM camera 104 may be used by the healthcare provider to guide the elongated tool during the biopsy procedure. For example, with respect to FIG. 11, the first and/or second NM cameras 102, 104 may image the elongated tool 230 as the elongated tool 230 is advanced toward the lesion 114. In some embodiments, the elongated tool 230 may include a radioactive source that is detected by the second NM camera 104 when the elongated tool 230 is within the breast 110. By way of example, the radioactive source may be a wire or thin rod comprising Co-57 that is within the elongated tool 230. The wire or rod may extend to a distal end of the elongated tool 230. Detection of the radioactive source may verify that a portion of the elongated tool 230 has been positioned within or along the lesion 114.

In a similar manner, the second NM camera 104 may be used to guide the elongated tool 240 of FIG. 12. Alternatively or in addition to the second NM camera 104, the first NM camera 102 may be used to guide the elongated tool 240 during the lateral biopsy procedure. In some case, it may not be possible to effectively image the elongated tool as the elongated tool is inserted into the breast. In such embodiments, the biopsy procedure may be performed using a separate imaging device (e.g., ultrasound probe, small NM camera, other imaging modality). In other embodiments, a depth detection assembly may be used, such as the depth detection assembly 300 shown in FIG. 13. The biopsy procedure may also be performed without guidance based on the known 3D location of the lesion 114.

Figure 13:
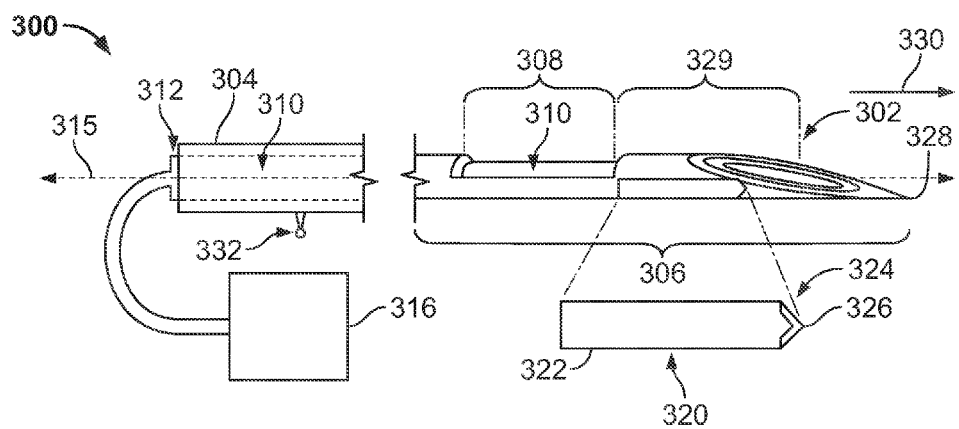
FIG. 13 is a side schematic view of a depth detection assembly in accordance with an embodiment that has an integrated gamma counter.

FIG. 13 illustrates a depth detection assembly 300 formed in accordance with an embodiment. The depth detection assembly 300 may be part of or used with the NM imaging system 100 (FIG. 1). The depth detection assembly 300 includes an elongated tool 302 having a proximal base 304, a leading end portion 306, and a central longitudinal axis 315 extending therebetween. The longitudinal axis 315 may extend through a geometric center of the elongated tool 302. In the illustrated embodiment, the elongated tool 302 is a biopsy needle that is configured to extract a sample of a lesion within a breast. The elongated tool 302 may have a length that is, for example, between about 9 cm and about 15 cm. In certain embodiments, the leading end portion 306 may have a diameter that is about 2.0 mm to about 4.5 mm or, more particularly, 2.5 mm to about 4.0 mm. In particular embodiments, the leading end portion 306 has a diameter that is between 2.75 mm and 3.5 mm.

The leading end portion 306 is configured to be inserted into patient tissue (e.g., a breast) and advanced toward a lesion in the patient tissue in an insertion direction 330. In particular embodiments, the leading end portion 306 includes an open-sided slot or notch 308. The open-sided slot 308 may have a length measured along the longitudinal axis 315 that is about 10 mm to about 20 mm. In particular embodiments, the length is about 14 to about 16 mm. The open-sided slot 308 may be in fluid communication with a channel 310 that extends through the leading end portion 306 and the proximal base 304. The channel 310 may have an opening 312 at the proximal base 304. In the illustrated embodiment, the opening 312 is located at a proximal end of the elongated tool 302. In other embodiments, however, the opening 312 may have a different position along the proximal base 304, such as along a side of the proximal base 304.

The proximal base 304 is configured to be located outside of the patient. The opening 312 is in fluid communication with the channel 310. In some embodiments, the depth detection assembly 300 may include a vacuum device 316 that is configured to provide a negative pressure within the open-sided slot 308 to draw a sample of a lesion into the open-sided slot 308. In some embodiments, the elongated tool 302 is configured to rotate when the sample is within the open-sided slot 308 thereby cutting the sample from the lesion. The elongated tool 302 may be manually rotated by an individual or rotated by an actuator (not shown).

The depth detection assembly 300 may also include an integrated gamma counter 320 that is coupled to the leading end portion 306 of the elongated tool 302. In the illustrated embodiment, the gamma counter 320 has a fixed location with respect to the elongated tool 302. The gamma counter 320 is configured to detect gamma photons (not shown) when the elongated tool 302 is inserted into the patient tissue. To this end, the gamma counter 320 includes a photon detector 322 having a detection surface 324 that generally faces in the insertion direction 330 when the elongated tool 302 is inserted into the patient tissue. The detection surface 324 is configured to detect gamma photons that are incident thereon.

The photon detector 322 may include one or more detector elements 326 that are capable of detecting gamma photons. The detector element 326 (or elements) includes the detection surface 324. By way of example, the detector elements 326 may be CZT elements. In the illustrated embodiment, the detector element 326 has a conical shape such that detection surface 324 receives gamma photons that are propagating parallel to the longitudinal axis 315 (in a direction opposite the insertion direction 330) and also gamma photons that have an angle with respect to the longitudinal axis 315, such as 90° or less. In other embodiments, the detection surface 324 may only face in a direction that is parallel to the longitudinal axis 315. Yet in other embodiments, the detection surface 324 may include multiple detector elements 326. The detector elements 326 may face parallel to the longitudinal axis 315 or may face in different directions. For embodiments that include multiple detector elements 326 facing in different directions, the gamma photons detected by each detector element 326 may be analyzed and compared to provide additional information regarding a location of the lesion.

The gamma counter 320 may have a fixed axial location with respect to the longitudinal axis 315. As shown in FIG. 13, the leading end portion 308 includes a distal end 328 of the elongated tool 302. The gamma counter 320 may be located (a) at the distal end 328, (b) within the open-sided slot 308, or (c) between the distal end 328 and the open-sided slot 308 (as shown in FIG. 13). In particular embodiments, the location of the detection surface 324 relative to the open-sided slot 308 is known. For example, the detection surface 324 is separated from the open-sided slot 308 by a separation distance 329 that is measured along the longitudinal axis 315.

Although not shown in FIG. 13, in some embodiments, the photon detector 322 may also include a collimator that is coupled to the detection surface 324 and configured to filter gamma photons approaching the detection surface 324 so that only gamma photons propagating generally parallel to the longitudinal axis 315 or other predetermined direction may be detected. For example, the collimator may have a hole that extends lengthwise in a direction parallel to the longitudinal axis 315. The collimator may include similar materials and have a similar construction as the collimators 124, 126 (FIG. 1).

The gamma counter 320 is configured to communicate radiation information based on a number of photons detected by the gamma counter 320. For example, the gamma counter 320 may be communicatively coupled to a transmitter 332 that communicates the radiation information. The NM imaging system 100 (FIG. 1) may include a receiver (not shown) that receives the radiation information. The radiation information may be communicated to the lesion-locator module 150 (FIG. 1). The radiation information may include a count rate that changes as the elongated tool 302 advances closer to or further from the lesion.

Figure 14:
FIG. 14 illustrates a relationship between a count rate of gamma photons and a distance between the lesion and the gamma counter of FIG. 13.

FIG. 14 includes a graph 340 illustrating a relationship between a count rate 342 detected by the gamma counter 320 (FIG. 13) and a distance between the detection surface 324 (FIG. 13) and a lesion. The count rate 342 is based on the number of gamma photons detected by the gamma counter 320 within a predetermined time. In particular embodiments, the lesion-locator module 150 (FIG. 1) may monitor the count rate 342 (or similar measurement) as the elongated tool 302 (FIG. 13) is inserted into the patient tissue in the insertion direction 330 (FIG. 13).

As the detection surface 324 approaches the lesion, the count rate 342 may increase. When the detection surface 324 clears the lesion, the count rate 342 may decrease. The lesion-locator module 150 may monitor the count rate 342 and identify when an inflection 344 in the count rate 342 occurs. The inflection 344 may represent a point at which the count rate 342 transitions from an increasing rate to a decreasing rate. The inflection 344 may represent a maximum value of the count rate 342. After identifying the inflection 344, an operator of the depth detection assembly 300 may extract the sample of the lesion. Depending upon the separation distance 329 (FIG. 13) between the detection surface 324 and the open-sided slot 308 and dimensions of the open-sided slot 308, the operator may choose to adjust the depth of the open-sided slot 308 prior to extracting the sample. More specifically, the open-sided slot 308 may be inserted deeper into the patient tissue or may be partially withdrawn to a shallower location.

With respect to the illustrated embodiment shown in FIG. 13, the detection surface 324 is located between the distal end 328 and the open-sided slot 308. More specifically, the detection surface 324 is located in front of the open-sided slot 308 by the separation distance 329. The separation distance 329 may be sufficient so that the operator may identify the inflection 344 (FIG. 14) and, upon identifying the inflection 344, cut the sample from the lesion without adjusting a depth of the open-sided slot 308. In other words, the separation distance 329 may be sufficient to confirm with a reasonable degree of certainty that the detection surface 324 has cleared the lesion without the open-sided slot 308 clearing the lesion. To extract the sample, the vacuum device 316 may be activated to draw the sample into the open-sided slot 308 and the elongated tool 302 may be rotated to cut the sample free of the lesion.

Figure 15:
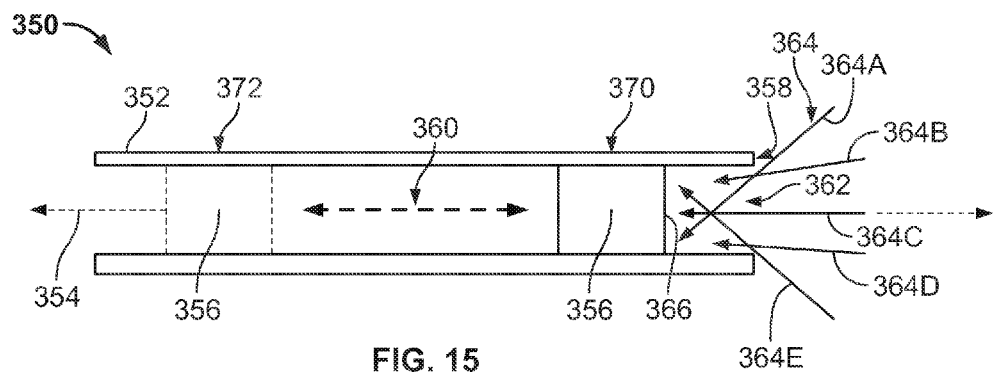
FIG. 15 is a side schematic view of a portion of a depth detection assembly in accordance with an embodiment that has a movable gamma counter.

FIG. 15 is a schematic diagram of a portion of a depth detection assembly 350 that may be similar to the depth detection assembly 300 (FIG. 13) and may be used with the NM imaging system 100 (FIG. 1). The depth detection assembly 350 includes an elongated tool 352, which may be, for example, an introducer or biopsy needle. The elongated tool 352 may be oriented with respect to a central longitudinal axis 354 that extends through a geometric center of the elongated tool 352. The depth detection assembly 350 includes a photon detector 356 that is movable along the longitudinal axis 354. The photon detector 356 is located within a channel 360 of the elongated tool 352. The elongated tool 352 includes a distal end 358 that is configured to face a lesion when the elongated tool 352 is inserted into the patient tissue. The elongated tool 352 includes an opening 362 that is configured to receive gamma photons 364. The material of the elongated tool 352 that defines the opening 362 proximate to the distal end 358 may be configured to block the gamma photons 364.

The photon detector 356 is configured to be moved to and from the distal end 358 between a distal location 370 and a proximal location 372. By way of example, the photon detector 356 may be moved pneumatically and/or by a guidewire (not shown). The photon detector 356 includes a detection surface 366. As the photon detector 356 is moved to and from the distal end 358, the number of photons that are incident on the detection surface 366 may change. For example, when the detection surface 366 is at the distal location 370, each of gamma photons 364A, 364B, 364C, 364D, and 364E are detected by the photon detector 356. However, if the photon detector 356 is at the proximal location 372, only gamma photons 364B-364D would be detected while other gamma photons would be blocked by the material of the elongated tool 302. The count rate of the photon detector 356 at the proximal location may be less than the count rate of the photon detector 356 at the distal location. In some embodiments, the count rates at the distal location 370 and the proximal location 372 may be analyzed and compared by the lesion locator module 150 (FIG. 1) to provide information regarding a size of the lesion and/or a location with respect to the distal end 358.

Figure 17:
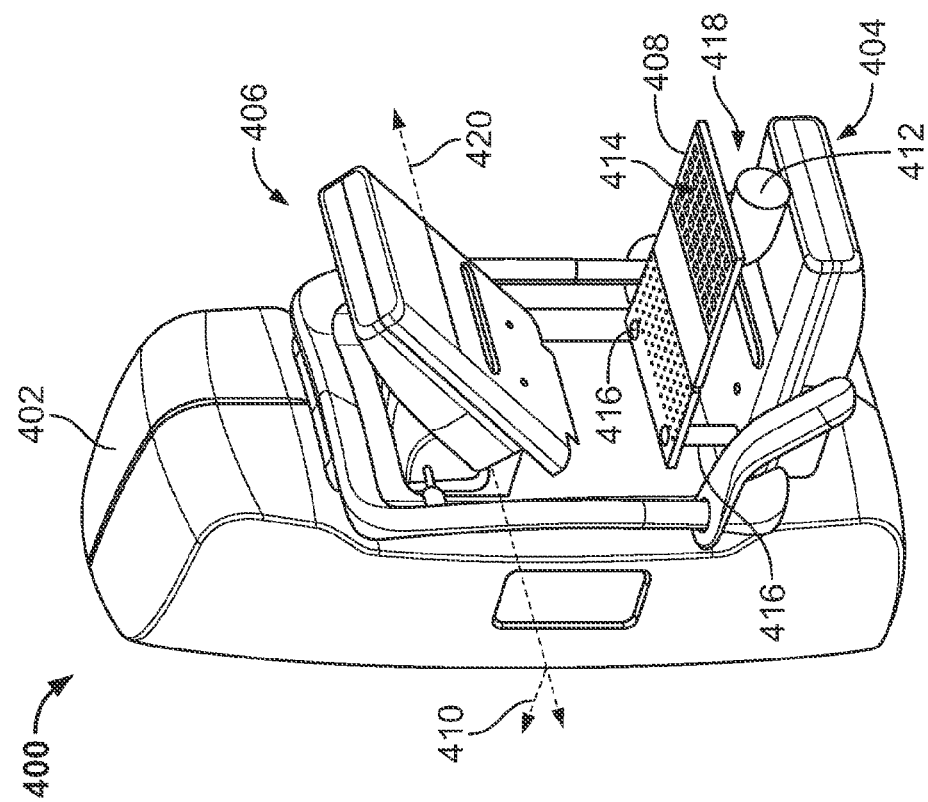
FIG. 17 is a perspective view of the NM imaging system of FIG. 16 with a movable NM camera positioned away from an immobilization plate.
Figure 16:
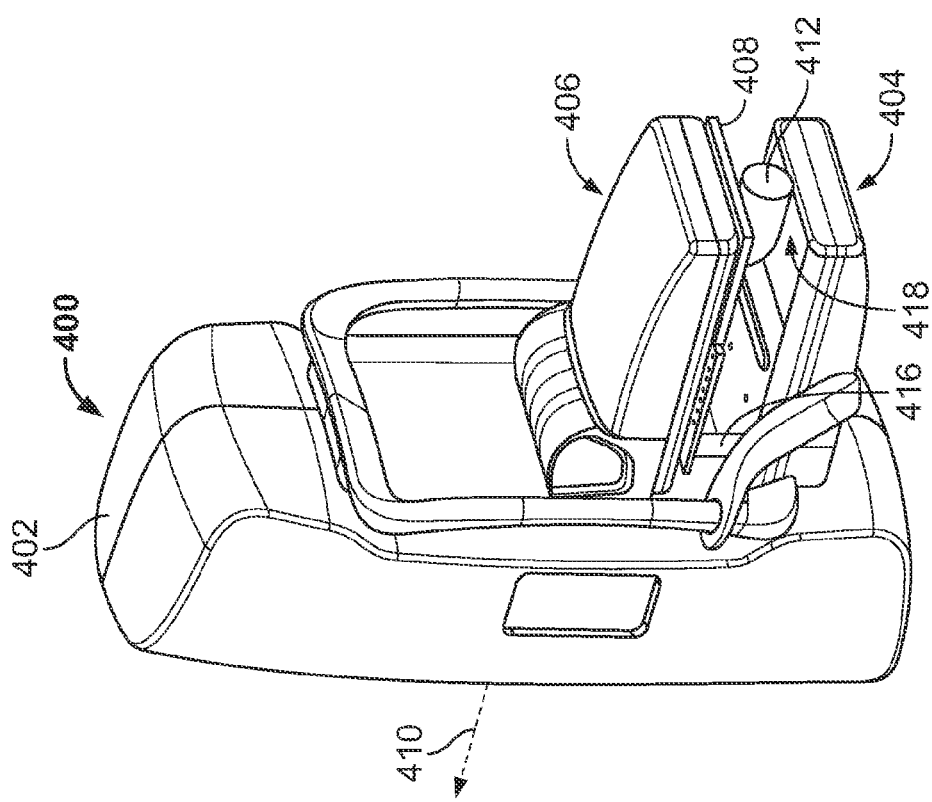
FIG. 16 is a perspective view of a portion of an NM imaging system in accordance with an embodiment during a 2D-acquisition stage.

FIGS. 16 and 17 are perspective views of a portion of an NM imaging system 400 that includes a movable base 402, a first NM camera 404, a second NM camera 406, and an immobilization plate 408 positioned between the first and second NM cameras 404, 406. A breast 412 is positioned between the immobilization plate 408 and the first NM camera 404. FIG. 16 shows the NM imaging system 400 during an initial 2D-acquisition stage, and FIG. 17 shows the NM imaging system 400 when the second NM camera 406 has been moved away from the immobilization plate 408 and rotated about a pitch axis 420.

The movable base 402 is configured to be coupled to a gantry (not shown) and rotatable about a system axis 410. Each of the first NM camera 404, the second NM camera 406, and the immobilization plate 408 is coupled to the movable base 402 such that the first and second NM cameras 404, 406 and the immobilization plate 408 move with the movable base 402 when the movable base 402 is rotated about the system axis 410 while maintaining the same spatial relationships with respect to one another.

The immobilization plate 408 is substantially planar and includes a plurality of passages 414 (FIG. 17) extending therethrough. The immobilization plate 408 is directly coupled to adjustable posts 416. The adjustable posts 416 are capable of being moved to change dimensions of a gap 418 between the immobilization plate 408 and the first NM camera 404. A height of the adjustable posts 416 may be monitored (e.g., by a motion-control module communicatively coupled to a sensor) to determine a distance between the immobilization plate 408 and the first NM camera 404.

Figure 18:
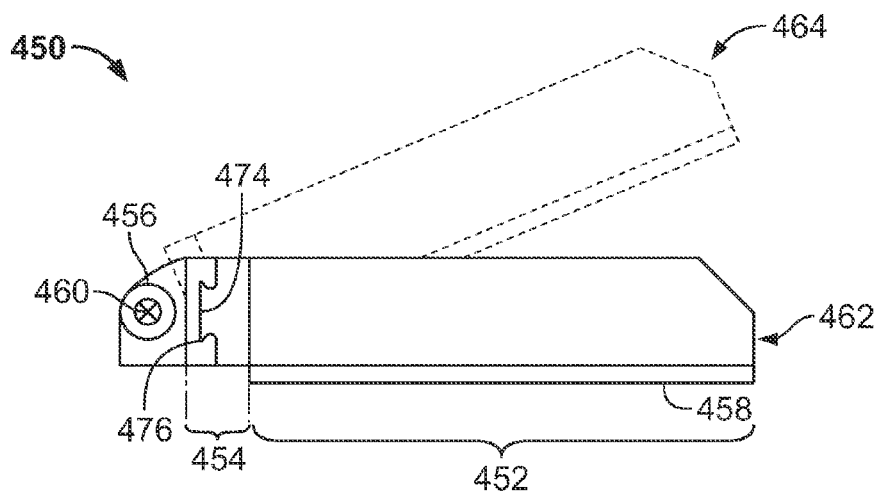
FIG. 18 is a side view of the movable NM camera of the NM imaging system of FIG. 16.
Figure 19:
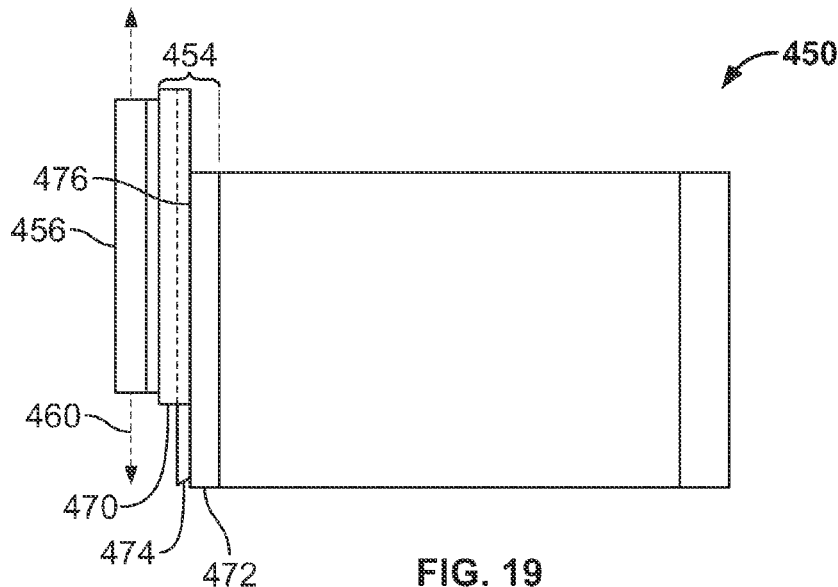
FIG. 19 is a top-down view of the movable NM camera of the NM imaging system of FIG. 16 having a first rotational orientation.
Figure 20:
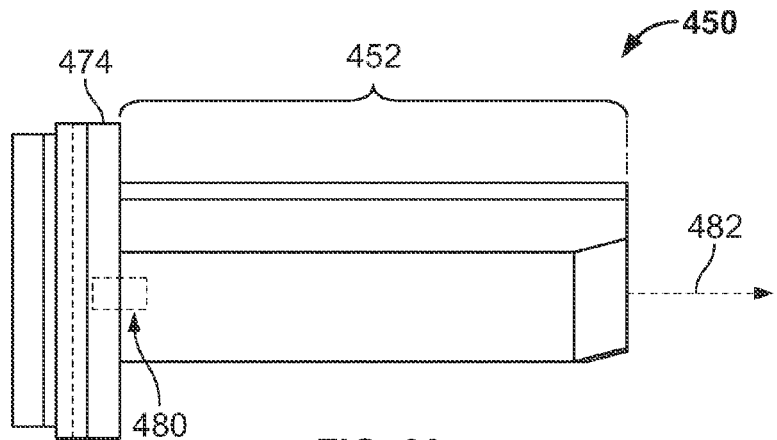
FIG. 20 is a top-down view of the movable NM camera of the NM imaging system of FIG. 16 having a second rotational orientation.

FIGS. 18-20 show different views of a movable NM camera 450 and illustrates the various movements that the movable NM camera 450 may achieve to position the NM camera 450 in a designated position. The movable NM camera 450 may be similar to the second NM camera 104 (FIG. 1) or the second NM camera 406 (FIG. 16).

FIG. 18 is a side view of the NM camera 450. The NM camera 450 includes an imaging portion 452, a sliding device 454, and an axle 456. The imaging portion 452 includes a camera surface 458 that is configured to face patient tissue (not shown) during an imaging session. The axle 456 is configured to be secured to a movable base (not shown) and/or a gantry (not shown) at one or both ends of the axle 456. The axle 456 coincides with a pitch axis 460. As shown in FIG. 18, the NM camera 450 is configured to rotate about the pitch axis 460 in a counter-clockwise direction from an imaging position 462 to an inclined or pitched position 464. In some embodiments, the NM camera 450 may also be capable of rotating in a clockwise direction from the imaging position 462 to another inclined position (not shown).

FIG. 19 is a top-down view of the movable NM camera 450 when the movable NM camera 450 has been moved laterally along the pitch axis 460. The sliding device 454 may include first and second plates 470, 472 that are coupled to each other and have complementary shapes that permit a sliding motion of the imaging portion 452 along the pitch axis 460. More specifically, the imaging portion 452 may be secured to the second plate 472 and first plate 470 may be secured to the axle 456. The second plate 472 may have a dovetail joint 474 (also shown in FIG. 18) that is received by a complementary recess 476 (also shown in FIG. 18) of the first plate 470. The dovetail joint 474 and the recess 476 may interact to permit later movement of the imaging portion 452.

FIG. 20 is a top-down view of the movable NM camera 450 when the movable NM camera 450 is oriented to have a non-orthogonal relationship with respect to an immobilization plate (not shown). As shown, the imaging portion 452 and the second plate 472 may form a rotatable joint 480 that permits the imaging portion 452 to be rotated about a roll axis 482. The rotatable joint 480 may include a motor (not shown) for moving the imaging portion 452 and/or a sensor (not shown) for measuring an orientation of the imaging portion 452 with respect to the roll axis 482.

Accordingly, the movable NM camera 450 may be capable of various movements, including pitch, roll, and lateral movements, to achieve a designated position. In some embodiments, the movements are caused by an individual that manually moves the NM camera 450. Alternatively or in addition to manual movement, the NM imaging system may be capable of automatically moving the NM camera 450 into the designated position. The NM imaging system may also include one or more sensors for determining a position of the imaging portion 452.

Figure 21:
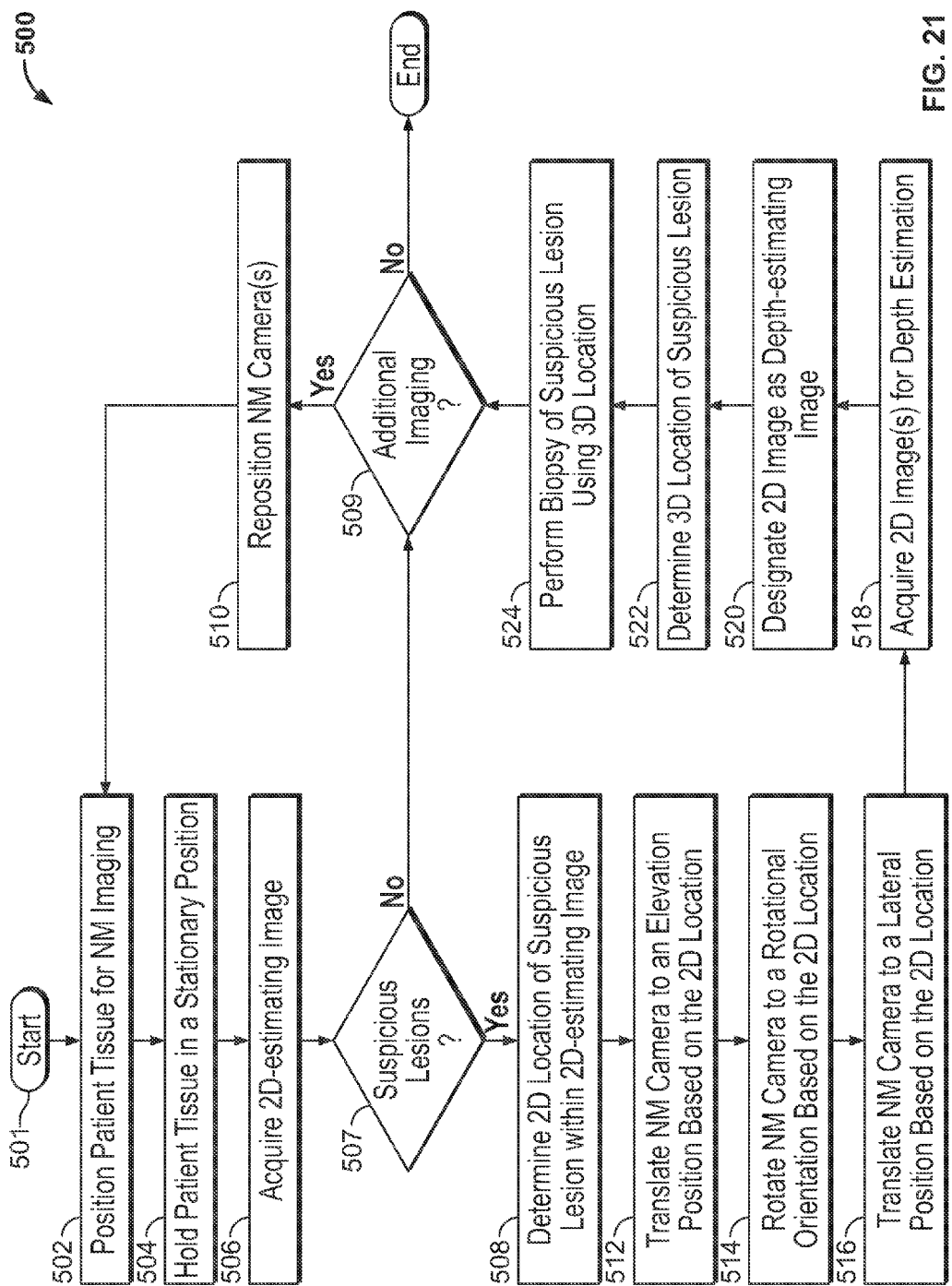
FIG. 21 is a flow chart illustrating a method of imaging patient tissue using an NM camera in accordance with an embodiment.

FIG. 21 is a flow chart illustrating a method 500 of imaging patient tissue using an NM camera in accordance with an embodiment. The method 500, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 500 may include positioning (at 502) tissue of a patient within an NM imaging system for acquiring NM images of the patient tissue. The method 500 may also include holding (at 504) the patient tissue in a stationary position using an immobilization plate. For example, the patient tissue may be compressed between a first NM camera and an immobilization plate. In some embodiments, a second NM camera may facilitate pressing the immobilization plate into the patient tissue. In particular embodiments, the patient tissue is breast tissue.

The method 500 also includes acquiring (at 506) at least one 2D-estimating image of the patient tissue in the stationary position. The 2D-estimating image may be acquired by at least one of the first and second NM cameras. At 507, it may be determined whether the 2D-estimating includes any suspicious lesions. For example, an operator of the NM imaging system may view the 2D-estimating image on a display and/or the NM imaging system may automatically analyze the 2D-estimating image to identify any suspicious lesions. If the 2D-estimating image includes a suspicious lesion, a 2D location of the lesion within the 2D-estimating image may be determined at 508. The 2D location may be determined by analyzing the 2D-estimating image as described above with respect to the lesion-locator module 150 (FIG. 1). Alternatively, the operator may manually mark the lesion on the display with a curser or other object.

If there are no suspicious lesions, it may be determined (at 509) whether to acquire additional 2D-estimating images along different imaging planes. If additional imaging is required, the first and second NM cameras may be repositioned (at 510). For example, the first and second NM cameras may be rotated with a movable base. In a first orientation of the movable base, each of the first and second NM cameras may face each other along a vertical axis. In a second orientation of the movable base, each of the first and second NM cameras may face each other along a horizontal axis. 2D-estimating images may be acquired in the first and second orientations for either breast.

If any suspicious lesions are detected at 507, the method 500 may include moving the second NM camera to a designated position for acquiring depth-estimating images. For example, the moving may include translating (at 512) the second NM camera to an elevation position, rotating (at 514) the NM camera so that an acute angle is formed between a camera surface of the second NM camera and the immobilization plate, and translating (at 516) the second NM camera to a lateral position. Each of the lateral position, the rotational orientation, and the elevation position may be based on the 2D location of the lesion in the 2D-estimating image. It should be noted that the translating (at 512), the rotating (at 514), and the translating (at 516) are only optional and may occur in any order or concurrently.

The method 500 may also include acquiring (at 518) a 2D image of the patient tissue in the stationary position while the acute angle exists between the second NM camera and the immobilization plate. In particular embodiments, acquiring (at 518) the 2D image of the patient tissue in the stationary position includes acquiring multiple 2D images at different lateral positions. For example, the second NM camera may be translated in a lateral direction that is parallel to the immobilization plate while a series of 2D images are acquired. The method 500 may also include designating (at 520) one of the 2D images as a depth-estimating image. The depth-estimating image may have the highest resolution of the suspicious lesion compared to other 2D images in the series.

The method 500 may also include analyzing (at 522) the depth-estimating image and the 2D-estimating image to determine a three-dimensional (3D) location of the lesion within the patient tissue. The depth of the suspicious lesion may be based on, at least in part, the acute angle and the 2D location of the suspicious lesion. The method 500 may also include performing (at 524) a biopsy of the suspicious lesion in which the biopsy procedure may be guided or based on the 3D location of the suspicious lesion.

Accordingly, various embodiments may provide one or more systems or methods of determining a 3D location of a lesion within patient tissue. Various embodiments may provide one or more systems or methods of guiding a biopsy device to the 3D location for extracting a sample of the lesion.

For example, in an embodiment, a nuclear medicine (NM) imaging system is provided that includes a gantry and first and second NM cameras coupled to the gantry. The first and second NM cameras have camera surfaces that are configured to face each other while imaging patient tissue therebetween. The NM imaging system also includes an immobilization plate that is configured to be positioned between the first and second NM cameras and extend parallel to the camera surface of the first NM camera. The immobilization plate is movable to and from the camera surface of the first NM camera to compress the patient tissue therebetween. The second NM camera is movable to and from the immobilization plate, wherein the second NM camera is oriented with respect to a roll axis that extends parallel to the immobilization plate. The second NM camera is rotatable about the roll axis while the immobilization plate and the first NM camera have fixed positions with respect to each other with the patient tissue compressed therebetween.

In an aspect, the second NM camera is configured to shift laterally in a direction parallel to the immobilization plate.

In another aspect, the second NM camera is oriented with respect to a pitch axis that extends parallel to the immobilization plate. The second NM camera is configured to rotate away from the immobilization plate about the pitch axis.

In another aspect, the first and second NM cameras are coupled to a movable base that is rotatable about a system axis that extends parallel to or coincides with the roll axis. The immobilization plate and the first and second NM cameras rotate with the movable base when the movable base is rotated about the system axis.

In another aspect, the first and second NM cameras are configured to acquire a 2D image and a depth-estimating image of the patient tissue in which the 2D image and the depth-estimating image extend along different imaging planes that are non-orthogonal with respect to each other. The NM imaging system also includes a lesion-locator module that is configured to analyze the 2D image and the depth-estimating image and determine a three-dimensional (3D) location of the lesion within the patient tissue.

In another aspect, at least one of the first and second NM cameras is configured to acquire a 2D image of the patient tissue during an image-acquisition stage. Optionally, during a depth-acquisition stage, the camera surface of the second NM camera is configured to be oriented non-orthogonal to the immobilization plate such that an acute angle is formed therebetween. The second NM camera is configured to acquire a depth-estimating image. The NM imaging system also includes a lesion-locator module that is configured to analyze the 2D image to determine a 2D location of a lesion within the patient tissue and analyze the depth-estimating image to determine a depth of the lesion. The depth of the lesion is based on the 2D location and the acute angle.

Optionally, the NM imaging system includes a lesion-locator module that is configured to analyze the 2D image to determine a 2D location of a lesion within the patient tissue. The second NM camera is configured to (a) automatically rotate about the roll axis to a designated rotational position such that an acute angle is formed between the camera surface of the second NM camera and the immobilization plate and (b) automatically shift laterally in a direction parallel to the immobilization plate so that the second NM camera has a designated lateral position with respect to the lesion. The designated rotational and lateral positions are based on the 2D location of the lesion.

In another aspect, the NM imaging system includes a lesion-locator module that is configured to receive radiation information from a biopsy needle having an integrated gamma counter advancing toward the lesion. The radiation information changes as the biopsy needle advances closer to or further from the lesion. The lesion-locator module is configured to analyze the radiation information to identify an inflection in a count rate of detected gamma photons.

In an embodiment, a depth detection assembly is provided that includes an elongated tool having a proximal base, a leading end portion, and a central longitudinal axis extending therebetween. The leading end portion is shaped to be inserted into patient tissue and advanced toward a lesion in the patient tissue. The depth detection assembly also includes a gamma counter that is secured to the leading end portion of the elongated tool. The gamma counter includes a detector and a collimator that is configured to receive gamma photons propagating generally parallel to the longitudinal axis. The gamma counter is configured to communicate radiation information based on a number of photons detected by the gamma counter.

In an aspect, the gamma counter has a fixed location along the longitudinal axis within the leading end portion.

In another aspect, the leading end portion includes an open-sided slot. The elongated tool includes a channel having an opening at the proximal base that is in fluid communication with the open-sided slot.

Optionally, the depth detection assembly may include a vacuum device that is configured to provide a negative pressure within the open-sided slot to draw a sample of the lesion into the open-sided slot.

In another aspect, the leading end portion includes a distal end of the elongated tool. The gamma counter is located (a) at the distal end, (b) within the open-sided slot, or (c) between the distal end and the open-sided slot.

In an embodiment, a method of imaging patient tissue using a nuclear medicine (NM) camera is provided. The method includes holding the patient tissue in a stationary position using an immobilization plate and acquiring a two-dimensional (2D) image of the patient tissue in the stationary position. The 2D image includes a lesion having a 2D location. The method also includes positioning the NM camera relative to the immobilization plate at a lateral position that is based on the 2D location of the lesion. The method also includes rotating the NM camera so that an acute angle is formed between a camera surface of the NM camera and the immobilization plate. The method also includes acquiring a depth-estimating image of the patient tissue in the stationary position while the acute angle exists between the NM camera and the immobilization plate.

In an aspect, the method includes determining a three-dimensional (3D) location of the lesion within the patient tissue based on the 2D image and the depth-estimating image.

In another aspect, a depth of the lesion is based on the acute angle and the 2D location of the lesion.

In another aspect, the NM camera has opposite camera sides that intersect the camera surface of the NM camera at corresponding side edges. One of the side edges is immediately adjacent to the immobilization plate when the acute angle exists and the other side edge is spaced apart from the immobilization plate.

In another aspect, acquiring the depth-estimating image of the patient tissue in the stationary position includes acquiring multiple depth-estimating images at different rotational positions of the NM camera.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical disk drive, and the like. The storage device may also be other similar means for loading computer programs or other instructions into the computer or processor.

As used herein, the terms "computer," "computing system," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the terms "computer," "computing system," or "module".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software, which may be a tangible non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A nuclear medicine (NM) imaging system comprising:
a gantry;
first and second NM cameras coupled to the gantry, the first and second NM cameras having first and second camera surfaces, respectively, that are configured to be parallel to each other such that the first and second NM cameras directly face each other while imaging patient tissue therebetween, wherein at least one of the first and second NM cameras is configured to acquire a 2D-estimating image of the patient tissue during an image-acquisition stage; and
an immobilization plate configured to be positioned between the first and second NM cameras and extend parallel to the first camera surface, the immobilization plate being movable to and from the first camera surface to compress the patient tissue, the second NM camera including a detector and a collimator that is coupled to the detector, the collimator having parallel holes that are perpendicular to the second camera surface, the second NM camera being movable to and from the immobilization plate, wherein the second NM camera is oriented with respect to an axis that extends parallel to the immobilization plate, the second NM camera being rotatable about the axis while the immobilization plate and the first NM camera have fixed positions with respect to each other with the patient tissue therebetween;
at least one processor configured to analyze the 2D-estimating image to determine a 2D location of a lesion within the patient tissue, the second NM camera being configured to shift laterally along the immobilization plate to move a side area of the second camera surface relative to the lesion, the side area being defined by a side edge of the second camera surface, wherein the second NM camera is configured to acquire a plurality of depth-estimating images in which the side edge of the second camera surface is adjacent to the immobilization plate, wherein, for each of the depth-estimating images, the side area of the second camera surface forms an acute angle with respect to the immobilization plate and has a lateral position that is based on the 2D location of the lesion, the second NM camera having different lateral positions for the plurality of depth-estimating images.

2. The NM imaging system of claim 1, wherein the axis is a roll axis and the second NM camera is oriented with respect to a pitch axis that extends parallel to the immobilization plate, the second NM camera configured to rotate away from the immobilization plate about the pitch axis.

3. The NM imaging system of claim 1, wherein the axis is a roll axis and the NM imaging system further comprises a movable base that is coupled to the gantry and has the first and second NM cameras coupled thereto, the movable base being rotatable about a system axis that extends parallel to or coincides with the roll axis, the immobilization plate and the first and second NM cameras rotating with the movable base when the movable base is rotated about the system axis.

4. The NM imaging system of claim 1, wherein the at least one processor is configured to determine a three-dimensional (3D) location of the lesion within the patient tissue based on the 2D-estimating image and at least one of the depth-estimating images.

5. The NM imaging system of claim 1, wherein the at least one processor is configured to identify a highest resolution image among the depth-estimating images and determine a depth of the lesion based on a designated position of the second NM camera when the highest resolution image was acquired.

6. The NM imaging system of claim 1, wherein the NM imaging system laterally positions the second NM camera for acquiring the depth-estimating images by commanding a motor to laterally shift the second NM camera.

7. The NM imaging system of claim 1, wherein the at least one processor is configured to receive position data that represents a rotational orientation of the second NM camera and the lateral position of the second NM camera for the depth-estimating images.

8. The NM imaging system of claim 1, wherein the at least one processor is configured to analyze at least one of the depth-estimating images of the second NM camera to determine a location of the lesion in an area of the at least one depth-estimating image that corresponds to the side area of the second camera surface.

9. A method of imaging patient tissue, the method comprising:
providing first and second nuclear medicine (NM) cameras, the first and second NM cameras having first and second camera surfaces, respectively, that are configured to be parallel to each other such that the first and second NM cameras directly face each other while imaging patient tissue therebetween, the second NM camera including a detector and a collimator that is coupled to the detector, the collimator having parallel holes that are perpendicular to the second camera surface;
holding the patient tissue in a stationary position between an immobilization plate and the first NM camera, the immobilization plate configured to be positioned between the first and second NM cameras and extend parallel to the first camera surface, the immobilization plate being movable to and from the first camera surface to compress the patient tissue;
acquiring a two-dimensional (2D)-estimating image of the patient tissue in the stationary position using at least one of the first NM camera or the second NM camera, the 2D-estimating image including a lesion having a 2D location;
shifting the second NM camera laterally along the immobilization plate to a first lateral position that is based on the 2D location of the lesion while the patient tissue is held in the stationary position;
rotating the second NM camera so that an acute angle is formed between the second camera surface and the immobilization plate;
acquiring a first depth-estimating image of the patient tissue in the stationary position while the acute angle exists between the second NM camera and the immobilization plate; and
shifting the second NM camera laterally along the immobilization plate to a second lateral position while the patient tissue is in the stationary position and acquiring a second depth-estimating image with the second NM camera in the second lateral position.

10. The method of claim 9, further comprising determining a three-dimensional (3D) location of the lesion within the patient tissue based on the 2D-estimating image and at least one of the first depth-estimating image or the second depth-estimating image.

11. The method of claim 9, wherein the second NM camera has opposite camera sides that intersect the second camera surface at corresponding side edges of the second camera surface, one of the side edges of the second camera surface being immediately adjacent to the immobilization plate when the acute angle exists and the other side edge of the second camera surface being spaced apart from the immobilization plate when the acute angle exists, wherein, for at least one of the first and second depth-estimating images, the lesion is detected by a side area of the second camera surface that is defined by the side edge that is immediately adjacent to the immobilization plate.

12. The method of claim 11, wherein the side area is at most one-fifth of the second camera surface.

13. The method of claim 12, the method further comprising imaging an elongated tool with the second NM camera during a biopsy procedure.

14. The method of claim 9, further comprising determining a depth of the lesion within the patient tissue based on at least one of the first depth-estimating image or the second depth-estimating image.

15. The method of claim 9, further comprising identifying a higher resolution image among the first and second depth-estimating images and determining a depth of the lesion within the patient tissue based on the higher resolution image.

16. A nuclear medicine (NM) imaging system comprising:
a gantry;
first and second NM cameras coupled to the gantry, the first and second NM cameras having first and second camera surfaces, respectively, that are configured to be parallel to each other such that the first and second NM cameras directly face each other while imaging patient tissue therebetween, wherein at least one of the first and second NM cameras is configured to acquire a 2D-estimating image of a lesion within the patient tissue during an image-acquisition stage; and
an immobilization plate configured to be positioned between the first and second NM cameras and extend parallel to the first camera surface, the immobilization plate being movable to and from the first camera surface to compress the patient tissue, the second NM camera including a detector and a collimator that is coupled to the detector, the collimator having parallel holes that are perpendicular to the second camera surface, the second NM camera being movable to and from the immobilization plate, wherein the second NM camera is oriented with respect to an axis that extends parallel to the immobilization plate, the second NM camera being rotatable about the axis while the immobilization plate and the first NM camera have fixed positions with respect to each other with the patient tissue therebetween;
wherein the second camera surface includes a side area that is defined by a side edge of the second camera surface, the second NM camera configured to shift laterally along the immobilization plate to a lateral position and configured to rotate about the axis to a rotational orientation in which the side edge of the second camera surface is adjacent to the immobilization plate and the side area of the second camera surface forms an acute angle with respect to the immobilization plate, the second NM camera configured to acquire a depth-estimating image at the lateral position and in the rotational orientation such that the side area detects the lesion.

17. The NM imaging system of claim 16, further comprising at least one processor that is configured to determine a three-dimensional (3D) location of the lesion within the patient tissue based on the 2D-estimating image and the depth-estimating image.

18. The NM imaging system of claim 16, wherein the NM imaging system is configured to move the second NM camera for acquiring the depth-estimating image by commanding a motor of the NM imaging system to laterally shift the second NM camera.

19. The NM imaging system of claim 16, wherein the depth-estimating image is a first depth-estimating image and the lateral position is a first lateral position, the second NM camera configured to move along the immobilization plate to a second lateral position and acquire a second depth-estimating image at the second lateral position.

20. The NM imaging system of claim 16, further comprising at least one processor that is configured to determine the lateral position and the rotational orientation of the second NM camera for the depth-estimating image based on a 2D location of the lesion.

* * * * *